(12) United States Patent
Rögner et al.

(10) Patent No.: US 11,802,271 B2
(45) Date of Patent: Oct. 31, 2023

(54) METHOD FOR IRRADIATING MAMMALIAN CELLS WITH ELECTRON BEAMS AND/OR X-RAYS

(71) Applicant: FRAUNHOFER-GESELLSCHAFT ZUR FÖRDERUNG DER ANGEWANDTEN FORSCHUNG E.V., Munich (DE)

(72) Inventors: Frank-Holm Rögner, Dresden (DE); Sebastian Ulbert, Leipzig (DE); Jana Burkhardt, Leipzig (DE); Javier Portillo, Dresden (DE); Jessy Schönfelder, Dresden (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 1070 days.

(21) Appl. No.: 16/494,728

(22) PCT Filed: Mar. 14, 2018

(86) PCT No.: PCT/EP2018/056393
§ 371 (c)(1),
(2) Date: Sep. 16, 2019

(87) PCT Pub. No.: WO2018/167149
PCT Pub. Date: Sep. 20, 2018

(65) Prior Publication Data
US 2020/0102539 A1  Apr. 2, 2020

(30) Foreign Application Priority Data
Mar. 17, 2017 (DE) .......................... 102017002645.9

(51) Int. Cl.
C12N 13/00 (2006.01)
C12N 5/0783 (2010.01)
A61K 35/17 (2015.01)

(52) U.S. Cl.
CPC ............ *C12N 5/0646* (2013.01); *A61K 35/17* (2013.01); *C12N 13/00* (2013.01); *C12N 2529/10* (2013.01)

(58) Field of Classification Search
CPC .. C12N 5/0646; C12N 13/00; C12N 2529/10; A61K 35/17
See application file for complete search history.

(56) References Cited

U.S. PATENT DOCUMENTS 8,173,139 B1   5/2012  McReynolds et al.
8,915,833 B1 * 12/2014  Sahadevan ........... A61N 5/1084
                                                    600/1
(Continued)

FOREIGN PATENT DOCUMENTS

CN   101366950 A   2/2009
EP   1854474 A1   11/2007
(Continued)

OTHER PUBLICATIONS

Carotta, Sebastian, "Targeting NK Cells for Anticancer Immunotherapy: Clinical and Preclinical Approaches," Frontiers in Immunology, Apr. 2016, vol. 7, Article No. 152, pp. 1-10.
(Continued)

*Primary Examiner* — David W Berke-Schlessel
*Assistant Examiner* — Trent R Clarke
(74) *Attorney, Agent, or Firm* — Melissa Hunter-Ensor; Leslie Serunian; Greenberg Traurig, LLP

(57) ABSTRACT

The present invention relates to a method for irradiating a population of mammalian cells comprising at least one target mammalian cell with electron beams and/or X-rays,
(Continued)

Figure 1:
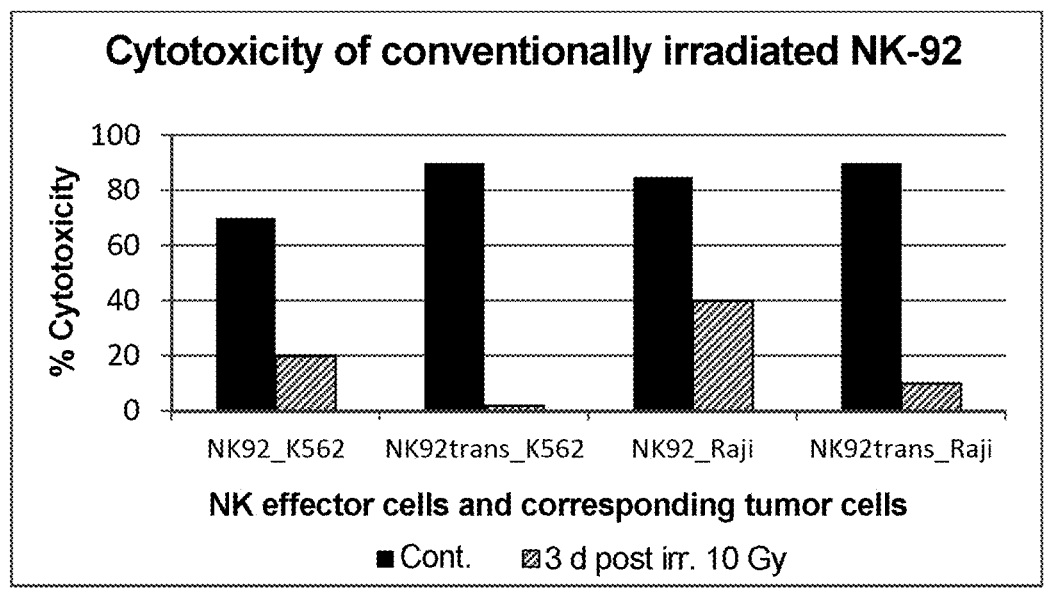
Figure 1:
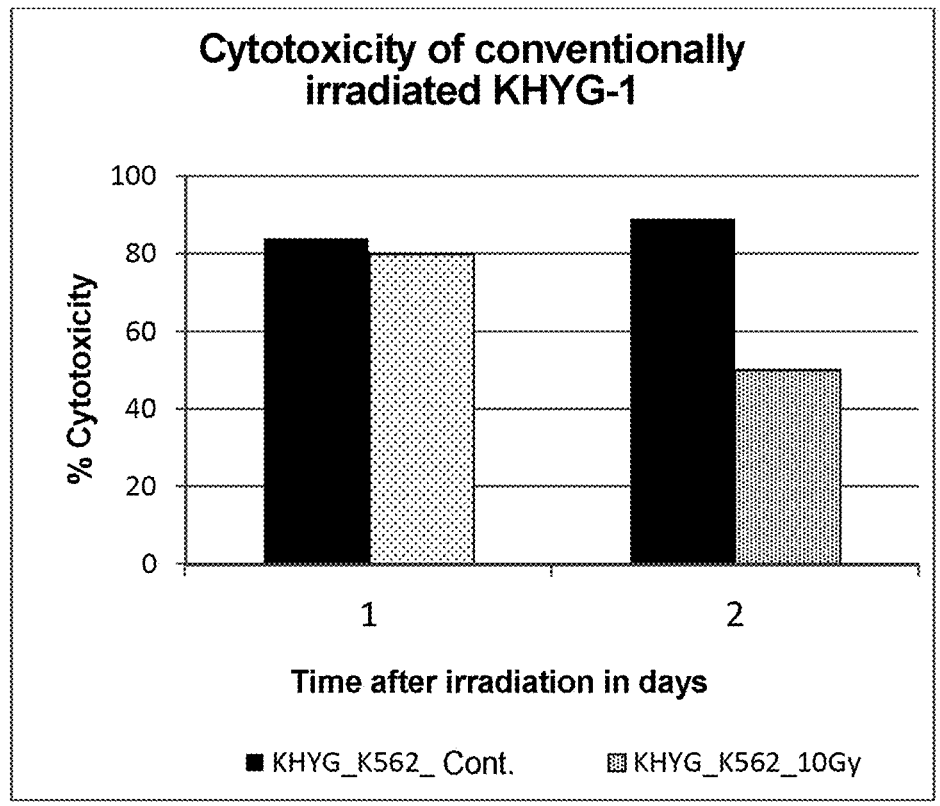

characterized in that: (i) a composition comprising a population of mammalian cells is irradiated in vitro with electron beams and/or X-rays, the population of mammalian cells containing at least one target mammalian cell and the dose rate being within the range from 5 Gy/sec to $10^7$ Gy/sec, and (ii) optionally viable target mammalian cells are isolated or enriched from the population of mammalian cells, and to agents obtainable thereby and to uses thereof.

17 Claims, 12 Drawing Sheets

(56) References Cited

U.S. PATENT DOCUMENTS

2010/0003316 A1   1/2010   Dinh et al.
2010/0255578 A1*  10/2010  Muraki ............... A61P 37/02
                                                    435/372

FOREIGN PATENT DOCUMENTS

WO   2015011265 A1   1/2015
WO   2017017184 A1   2/2017

OTHER PUBLICATIONS

De Andrade et al., "Gamma irradiation preserves immunosuppressive potential and inhibits clonogenic capacity of human bone marrow-derived mesenchymal stromal cells," Journal of Cellular and Molecular Medicine, 2014, vol. 18, No. 6, pp. 1184-1193.
De-Yu et al., "The Impact of X-ray Irradiation on Lymphocyte Proliferation and NK Cells Activity in Cord Blood," China Cancer, 2005, vol. 14, pp. 376-378.
De-Yu et al., "The Impact of X-ray Irradiation on Lymphocyte Proliferation and NK Cells Activity in Cord Blood," China Cancer, 2005, vol. 14, pp. 376-378. [Translation].
Fertey et al., "Pathogens Inactivated by Low-Energy-Electron Irradiation Maintain Antigenic Properties and Induce Protective Immune Responses," Viruses, Nov. 23, 2016, vol. 8, Iss. 11, Article No. 319, pp. 1-14.
Fujisaki et al., "Expansion of Highly Cytotoxic Human Natural Killer Cells for Cancer Cell Therapy," Cancer Research, May 2009, vol. 69, No. 9, pp. 4010-4017.
Klingemann et al., "A cytotoxic NK-cell line (NK-92) for ex vivo purging of leukemia from blood," Biology of Blood and Marrow Transplantation: Journal of the American Society for Blood and Marrow Transplantation, 1996, vol. 2, No. 2, pp. 68-75.
Melief et al., "Summit on cell therapy for cancer: The importance of the interaction of multiple disciplines to advance clinical therapy," Journal of Translational Medicine, Jul. 8, 2011, vol. 9, No. 107, pp. 1-5.
Nold et al., "Immunosuppressive capabilities of mesenchymal stromal cells are maintained under hypoxic growth conditions and after gamma irradiation," Cytotherapy, Feb. 1, 2015, vol. 17, No. 2, pp. 152-162.
Suck et al., "Irradiated KHYG-1 retains cytotoxicity: Potential for adoptive immunotherapy with a natural killer cell line," International Journal of Radiation Biology, May 2006, vol. 82, No. 5, pp. 355-361.
Suck et al., "NK-92: an 'off-the-shelf therapeutic' for adoptive natural killer cell-based cancer immunotherapy," Cancer Immunology, Immunotherapy, 2016, vol. 65, No. 4, pp. 485-492.
Takahashi et al., "Induction of CD8+ cytotoxic T cells by immunization with purified HIV-1 envelope protein in ISCOMs," Nature, Apr. 26, 1990, vol. 344, pp. 873-875.
Tam et al., "Characterization of Genetically Altered, Interleukin 2-Independent Natural Killer Cell Lines Suitable for Adoptive Cellular Immunotherapy," Human Gene Therapy, May 20, 1999, vol. 10, No. 8, pp. 1359-1373.
Vandenberk et al., "Irradiation of necrotic cancer cells, employed for pulsing dendritic cells (DCs), potentiates DC vaccine-induced antitumor immunity against high-grade glioma," OncoImmunology, Feb. 26, 2016, vol. 5, No. 2, e1083669, pp. 1-15.
Yagita et al., "A novel natural killer cell line (KHYG-1) from a patient with aggressive natural killer cell leukemia carrying a p53 point mutation," Leukemia, 2000, vol. 14, No. 5, pp. 922-930.
International Search Report, dated May 18, 2018, in corresponding International Patent Application No. PCT/EP2018/056393 (3 pages).

* cited by examiner

A)

B)

A)

B)

A)

B)

A)

B)

a) NK92 viability after conventional irradiation b) NK92 viability after minimum-dose electron beam irradiation a)

b)

a)

b)

a) KHYG1 viability after conventional irradiation b) KHYG1 viability after minimum-dose electron beam irradiation a)

b)

a)

b)

METHOD FOR IRRADIATING MAMMALIAN CELLS WITH ELECTRON BEAMS AND/OR X-RAYS

CROSS-REFERENCE TO RELATED APPLICATIONS

This application is the U.S. national phase application, pursuant to 35 U.S.C. § 371, of PCT International Application Ser. No.: PCT/EP2018/056393, filed Mar. 14, 2018, designating the United States and published in English, which claims the benefit of European Patent Application No.: 102017002645.9, filed Mar. 17, 2017, the entire contents of which are incorporated herein by reference.

The present invention relates to a method for irradiating a population of mammalian cells comprising at least one target mammalian cell with electron beams and/or x-rays, characterized in that: (i) a composition comprising a population of mammalian cells is irradiated in vitro with electron beams and/or x-rays, wherein the population of mammalian cells contains at least one target mammalian cell, and wherein the dose rate is in the range of 5 Gy/sec to $10^7$ Gy/sec, and (ii) optionally, viable target mammalian cells are isolated or enriched from the population of mammalian cells, and to agents obtainable thereby and uses thereof.

Cellular therapeutic agents can be used for the treatment of various diseases. At present, the research status and clinical use of cellular therapeutic agents in the area of cancer treatment (Melief et al. 2011) is particularly promising.

In the past, however, a series of problems was seen in the use of this group of therapeutic agents. On the one hand, in order to obtain therapeutic cells, one must frequently use donor cells, which must be obtained in sufficient amounts and in accordance with clinical requirements. On the other hand, so-called autologous preparations, which are derived from the patient, are sometimes sharply limited in their potential effectiveness, particularly in the case of previously treated cancer patients.

An alternative is the use of cell lines which for example are derived from primary tumors or immortalized by means of viral treatment. Such cell lines can potentially be produced in any desired amounts and are therefore also suitable as an "on the shelf" product. In particular, cell lines corresponding to the characteristics of natural killer cells (NK cells) are already in clinical use for the treatment of tumors (Carotta 2016; Suck et al. 2016).

The therapeutic use of the cell lines NK-92 and KHYG-1 is of particular interest. These were originally lymphoma or leukemia cells that were taken from patients in the 1990s and continuously cultured (Klingemann et al. 1996; Yagita et al. 2000). Both of these cell lines have a profile corresponding to NK cells, can be stimulated for example by interleukin (IL) 2, and possess outstanding cytotoxic properties with respect to various tumor entities.

Furthermore, the use of these and other cellular products in patients is subject to stringent safety requirements. As these are cancer cells in principle, their growth must be inhibited prior to administration. Moreover, in the use of other cellular therapeutic agents as well, unhindered proliferation is usually accompanied by sometimes serious side effects such as the above-mentioned oncogenic potential, but also immunotoxic effects. These side effects must be avoided at all costs.

At present, a large number of cytotherapeutic products, in particular those originating from cancer cell lines, are therefore inactivated using gamma irradiation (Tam et al. 1999). This type of irradiation leads to complete inhibition of cell growth, and ultimately, after a certain period of time, as a rule a few days, to the death of the cells treated in this manner. In particular, gamma radiation is also known for its negative influence on functional efficacy, for example the anti-tumor cytotoxic activity of NK cells (FIG. 1).

Relevant examples of cellular therapeutic products that are inactivated by gamma irradiation prior to application include the following:

(a) irradiation of NK cell lines prior to use in cancer treatment (Klingemann et al. 1996)

(b) irradiation of so-called feeder cells, i.e. cell lines that are used for cultivating the actual therapeutic cell products, for example in the production of primary NK cell products (Fujisaki et al. 2009)

(c) irradiation of tumor cells ex vivo in the production of so-called cell vaccines based on dendritic cells (DCs) (Vandenberk et al. 2016)

(d) irradiation of other cell products, for example mesenchymal stromal cells, in order to prevent undirected proliferation or immunotoxic expansion in cellular immunosuppressive therapy (de Andrade, Ana Valeria Gouveia et al. 2014).

All of these cellular products are ordinarily irradiated ex vivo, i.e. before use in the patient and outside of the body, with gamma radiation at a high, ultimately lethal dose, usually approximately 10 to 50 Gy, and typically 30 Gy.

A highly relevant problem arising from this methodology of the prior art is the accompanying considerable loss of efficacy of the cellular therapeutic agents because of this unavoidable irradiation.

For example, NK-92 cells subjected to this type of gamma irradiation lose at least 50% of their cytotoxic potential (Tam et al. 1999).

NK cell lines that are genetically modified and optimized for tumor therapy are now also being produced, but these appear to be even more sensitive to radiation than unmodified NK cells.

This loss of efficacy is attributable on the one hand to frequently long irradiation times, which are required in order to reach high doses, but also to the accumulation of gamma irradiation-associated effects, such as undesired oxidation of effector molecules.

Moreover, the technical implementation of gamma irradiation of cell products is also sometimes problematic, because it requires strict shielding and safety measures, and decay radiation is generally more difficult to control from a technical standpoint (WO 2015/011265 A1).

The use of electron beam devices for the sterilization of solids and liquids has been described in the prior art. The use of electron beams has also been disclosed in connection with the production of vaccines based on irradiated viral particles (U.S. Pat. No. 8,173,139 B1; WO 2015/011265A1).

There is therefore a need for methods that are safe from a regulatory standpoint and easy to manage for producing cellular agents that are suitable for administration to an individual or for producing cellular agents that themselves are suitable for producing a cellular agent for administration to an individual, wherein said methods maintain the viability and biological activity of the irradiated cells, in particular for a long time after irradiation, such as 1 d to 7 d after irradiation, in the largest possible number of irradiated cells.

The problems of the prior art are solved by means of the methods according to the invention:

The present invention therefore relates in an embodiment to a method for irradiating a population of mammalian cells comprising at least one target mammalian cell with electron beams and/or x-rays, characterized in that:

(i) a composition comprising a population of mammalian cells is irradiated in vitro with electron beams and/or x-rays, wherein the population of mammalian cells contains at least one target mammalian cell, and wherein the dose rate is in the range of 5 Gy/sec to $10^7$ Gy/sec, and (ii) optionally, viable target mammalian cells are isolated or enriched from the population of mammalian cells.

The present invention therefore relates, in a further embodiment, to a method for producing an agent comprising at least one treated viable target mammalian cell that is suitable for administration to an individual and/or for producing treated viable target mammalian cells that are suitable for producing a cellular agent for administration to an individual, characterized in that:

(i) a composition comprising a population of mammalian cells is irradiated in vitro with electron beams and/or x-rays, wherein the population of mammalian cells contains at least one target mammalian cell, and wherein the dose rate is in the range of 5 Gy/sec to $10^7$ Gy/sec, and (ii) optionally, viable target mammalian cells are isolated or enriched from the population of mammalian cells.

Surprisingly, it was found that the proliferation capacity of the target mammalian cell can be reduced, for example completely inhibited, by irradiating a population of mammalian cells comprising at least one target mammalian cell with electron beams and/or x-rays at a high dose rate according to the invention, with the cells simultaneously remaining viable: surprisingly, compared to cells conventionally irradiated with x-ray or gamma radiation that were irradiated at a lower dose rate, the irradiated cell population shows a higher proportion of viable cells in the irradiated cell population for a long time after irradiation at the same radiation dose. In particular, after irradiation according to the invention, the cells can show a higher desired biological activity, such as cytotoxicity, compared to conventionally irradiated cells.

The examples and accompanying FIGS. 2 to 12 show that irradiation according to the invention with electron beams at a high dose rate is superior to conventional irradiation with gamma rays or x-rays at a lower dose rate, with respect both to the viability of the cells and the desired biological activity of cytotoxicity, using the same dose respectively.

In conventional irradiation methods with gamma rays or x-rays known from the prior art, a lower dose rate is used, i.e. a specified dose is applied over a longer period of time.

A further advantage of both electron beam irradiation and x-ray irradiation, in particular compared to gamma irradiation, lies in their potential use close to the patient (bedside use) and/or high throughput use: as comparatively minimal shielding is required, it is possible to carry out the irradiation methods according to the invention decentrally in a conventional radiology unit of a hospital. This makes it possible to reduce costs and travelling time.

An additional advantage is the avoidance of the long-term concomitant oxidative effects of the gamma radiation due to the ionized atmosphere, which can also have a detrimental effect on the functionality of the irradiated biological, in particular cellular, components. However, with the brief dose application times in electron beam systems or x-ray systems, in both cases at the high dose rates according to the invention in the range of 5 Gy/sec to $10^7$ Gy/sec, such side effects are avoided by means of the short treatment time, for example in the millisecond range.

The use of electron beams and/or x-rays is therefore advantageous because of the precise controllability of the desired high dose rate and the reduced safety risk to the operator and the environment of such a device compared to gamma rays, which are based on the decay of radionuclides.

In the method according to the invention, mammalian cells are irradiated. These mammalian cells may be cells from any desired mammal, including humans, pigs, cows, horses, dogs, cats, sheep, monkeys, rats, mice, rabbits, guinea pigs, or hares. In a particularly preferred embodiment, the mammal is a monkey or a human, most preferably a human. The mammalian cells may be cells taken directly from the mammal, primary cells, cultivated mammalian cells, or genetically modified mammalian cells, such as cell lines of mammalian cells. Immortalized cell lines, such as the immortalized cancer cell lines used in the examples, are a preferred embodiment of such cell lines.

The mammalian cells may be cells taken from various sites of a mammal, and for example can be blood cells, PBMC cells, plasma cells, tumor cells, cells from healthy or diseased tissue, cells from organs, such as liver cells, kidney cells, spleen cells, pancreatic cells, hematopoietic stem cells, cells from body fluids such as urine, saliva, or cerebrospinal fluid, and/or cells intended for transplantation.

Stem cells are preferably not human embryonal stem cells, and/or the population of mammalian cells preferably contains no human embryonal stem cells.

In these methods, a population of mammalian cells is irradiated. A population of mammalian cells comprises at least 2 cells, and preferably at least 3, 4, 5, 6, 7, 8, 9, 10, $10^2$, $10^3$, $10^4$, $10^5$, $10^6$, $10^7$, $10^8$, or $10^9$ cells, for example $10^2$ to $10^9$ cells, $10^3$ to $10^8$ cells, $10^4$ to $10^8$ cells, or $10^5$ to $10^7$ or $10^8$ to $10^9$ cells.

The population of mammalian cells contains at least one target mammalian cell. A target mammalian cell is a mammalian cell whose proliferation capacity is to be reduced by irradiation, while the viability of the target mammalian cell should be maintained for a period of 1 d to 7 d after irradiation, and preferably, the biological activity of the target mammalian cell should be maintained for a period of 1 d to 7 d after irradiation. Preferably, the viability of the target mammalian cell is maintained for 3 d after irradiation in at least 10%, 20%, 30%, 40%, 50%, 60%, 70%, or 80% of a majority of irradiated target mammalian cells and/or the biological activity of the target mammalian cell 3 d after irradiation is at least 10%, 20%, 30%, 40%, 50%, 60%, 70%, 80%, or 90% of the biological activity of the same mammalian cell not subjected to irradiation, with all of the other conditions being the same. It is possible for the population of mammalian cells to be composed of target mammalian cells or for the population of mammalian cells to contain at least one target mammalian cell and one or a plurality of other mammalian cells.

For example, it is possible to irradiate a cultivated immortalized mammalian cell line or tumor cells as target mammalian cells. In this embodiment, the population of mammalian cells can consist of target mammalian cells. In this embodiment, the population of mammalian cells contains no or essentially no other mammalian cells.

A population of mammalian cells that contains one or a plurality of other mammalian cells in addition to the target mammalian cell(s) can for example be a transplant comprising different cell types, such as a hematopoietic stem cell transplant, or a co-culture of 2, 3, or more different cell types of mammalian cells. For example, feeder cells can be contained in a co-culture comprising the feeder cells and the target mammalian cells, such as tumor cells.

In a preferred embodiment, a method according to the invention is therefore characterized in that the population of mammalian cells is composed of target mammalian cells or is essentially composed of target mammalian cells.

In a further preferred embodiment, a method according to the invention is therefore characterized in that the population of mammalian cells contains at least one target mammalian cell and one or a plurality of other mammalian cells.

In a further preferred embodiment, a method according to the invention is characterized in that the population of mammalian cells comprises a mixture of at least 2 different primary mammalian cells, in particular wherein the population of mammalian cells is a cellular transplant or a mixture of immune cells or a body fluid.

Primary mammalian cells are mammalian cells that were taken from a mammal and have maintained their phenotypic characteristics. Immortalized cells are not primary mammalian cells.

A mixture of immune cells can for example be a composition that contains one or a plurality of the following cells: T cells, in particular $T_{reg}$ cells, $CD4^+$ cells or $CD8^+$ T cells, NK cells, B cells, or DC cells.

A body fluid can for example be blood, blood plasma, whole blood, urine, saliva, or cerebrospinal fluid.

A cellular transplant can for example be a hematopoietic stem cell transplant. Furthermore, a cellular transplant can for example be allogeneic or autologous.

In a further preferred embodiment, a method according to the invention is characterized in that the population of mammalian cells comprises one or a plurality of cell lines or is composed of one or a plurality of cell lines.

In a further preferred embodiment, a method according to the invention is characterized in that the target mammalian cell is a proliferating, hyperproliferative or immortalized target mammalian cell, in particular wherein the target mammalian cell is a cancer cell, a cancer cell line and/or an immune cell, in particular wherein the cell line is a natural killer cell (NK cell) line, a T cell line, or a genetically modified cell line, and/or the immune cells are natural killer cells (NK cells), T cells, or genetically modified immune cells.

In these cells, it is necessary in particular to reduce the proliferation capacity, if possible by 100%, in order to prevent undirected proliferation and/or immunotoxic effects in vivo. At the same time, it is important to maintain viability for a long time after irradiation in order to allow the cells to exert the desired therapeutic, preventive or cosmetic effect.

Irradiated mammalian cell lines such as the NK cell line used in the examples can subsequently be used in cancer therapy, as harmful unhindered proliferation is reduced by the irradiation, while viability is maintained for a long period after irradiation.

In the same manner, the method can be used for so-called feeder cells as target mammalian cells. Feeder cells are cell lines used for cultivation of the actual therapeutic cell products, for example in the production of primary NK cell products.

According to the invention, tumor cells can also be irradiated that are used after treatment ex vivo in production of so-called cell vaccines based on dendritic cells (DCs).

However, other cellular agents, such as mesenchymal stromal cells, can also be irradiated as target mammalian cells. After irradiation according to the invention, which prevents undirected proliferation and immunotoxic expansion in vivo, such mesenchymal stromal cells can be used in cellular immunosuppressive therapy.

If one or a plurality of other mammalian cells are present in the population in addition to the target mammalian cell(s), the proliferation capacity of the one or plurality of other mammalian cells in the population can also be modified, in particular reduced, by the irradiation, and the viability can preferably be maintained for 1 d, 2 d, 3 d, 4 d, 5 d, 6 d, or 7 d after irradiation in at least 10%, 20%, 30%, 40%, 50%, 60%, 70%, or 80% of these mammalian cells. Preferably, the proliferation capacity of the one or plurality of other mammalian cells is reduced, while the viability is maintained for 1 d, 2 d, 3 d, 4 d, 5 d, 6 d, or 7 d after irradiation in at least 10%, 20%, 30%, 40%, 50%, 60%, 70%, or 80% of the cells, although this is not absolutely necessary. Such differences can result from different sensitivities of various cells to the radiation.

In an embodiment of the present invention, the method is for producing an agent comprising at least one treated viable target mammalian cell that is suitable for administration to an individual and/or for producing treated viable target mammalian cells that are suitable for producing a cellular agent for administration to an individual.

For example, immortalized cell lines can be irradiated according to the invention. A composition comprising viable cells of the cell line irradiated according to the invention can be administered to an individual as an agent for tumor therapy. An agent comprising viable cells of the cell line irradiated according to the invention that are reduced in their proliferation capacity, and preferably reduced in their proliferation capacity by 100%, is suitable for administration to an individual. In contrast, an agent is not suitable for administration to an individual if such administration leads to death or to disease of the individual without showing a predominant therapeutic effect. An agent is suitable for administration to an individual, in particular a human, if it is suitable for therapeutic, preventive, diagnostic, or cosmetic administration to an individual.

For example, feeder cells can be irradiated according to the invention. A composition comprising viable feeder cells irradiated according to the invention can be used for producing a cellular agent for administration to an individual. In this embodiment, the cellular agent can be a population of cells of a cell line. The feeder cells can be used for cultivation of the cellular agent, for example in the production of primary NK cell products. In this embodiment, the NK cell products are suitable and provided for administration to an individual.

A cellular agent is a composition comprising at least one viable cell, preferably a pharmaceutical or cosmetic composition comprising at least one viable cell, more preferably a pharmaceutical composition comprising at least one viable cell.

A cellular agent for administration to an individual is preferably sterile and/or contains no pyrogens.

An individual is a mammal, preferably a human.

In step (ii) of the methods according to the invention, viable target mammalian cells are optionally isolated or enriched from the population of mammalian cells.

For example, it is possible, if necessary, to isolate or enrich target mammalian cells after irradiation in step (i), for example by immunological methods such as apheresis, or centrifugation, filtering and washing, prior to administration to an individual.

The methods according to the invention are carried out in vitro using suitable devices for producing electron beams and/or x-rays. Such devices are known in the prior art.

Preferably, the method according to the invention is carried out using a device for the production of electron beams that operates in continuous or rapid-pulsed mode.

In a further preferred embodiment, the method according to the invention is carried out using a device for the production of electron beams that emits electrons according to the cold or hot cathode principle.

In a further preferred embodiment, the method according to the invention is carried out using a device for the production of electron beams that is configured as an axial irradiator (scanner) or a linear broadbrand irradiator.

In a further preferred embodiment of the method according to the invention, the composition is statically taken up in the device or continuously transported by the electron beam or x-ray beam.

Preferably, the method according to the invention is carried out using a device for the production of x-rays which, by means of a special target arrangement and a high-frequency deflected electron beam, provides the high dose rates according to the invention with high power density. Such devices for the production and high-frequency deflection of the electron beam are known in the prior art.

The methods according to the invention are carried out at a dose rate in the range of 5 Gy/sec to $10^7$ Gy/sec. Surprisingly, it was found that at this high dose rate, damage, in particular secondary damage, to the cells is minimized. With the method according to the invention, irradiated target mammalian cells are thus obtained that are viable for longer periods compared to conventionally irradiated mammalian cells, while the proliferation capacity of target mammalian cells can be simultaneously reduced (see FIGS. 2 to 12). In addition, the target mammalian cells irradiated by the method according to the invention preferably show higher biological activity over a longer period after irradiation compared to conventionally irradiated mammalian cells. In the case of NK cells, the biological activity is preferably cytotoxicity with respect to tumor cells. NK cells were successfully irradiated by the method according to the invention, as shown in the examples and FIGS. 2 to 12.

The dose rate (dose/time) can be suitably adjusted by the person skilled in the art. In general, it should be borne in mind that—with respect to a specified desired applied dose—a high beam current requires a short irradiation time, and a low beam current requires a long irradiation time. The dose rate is adjusted by the person skilled in the art taking into consideration, for example in continuous transport of the composition, the flow speed of the medium and the beam current range, which depends on the type of irradiator. By means of the high dose rate, a high applied dose in the composition can be achieved even with a short irradiation time.

According to the methods of the invention, irradiation is carried out (i) with electron beams, (ii) with electron beams and x-rays, or (iii) with x-rays, at a dose rate according to the invention in the range of 5 Gy/sec to $10^7$ Gy/sec.

In a preferred embodiment, the method is carried out with x-rays at a dose rate according to the invention in the range of 5 Gy/sec to $10^7$ Gy/sec.

In a further particularly preferred embodiment of the present invention, irradiation is carried out with electron beams at the dose rate according to the invention or with electron beams and x-rays at dose rates according to the invention, particularly preferably with electron beams at the dose rate according to the invention. It should be borne in mind that in irradiation with electron beams, x-ray radiation is also present at the point of incidence of the rays. For this reason, irradiation with electron beams also includes x-ray irradiation. However, the dose rate of the x-rays in irradiation with electron beams according to the invention will be markedly lower, approximately in the parts per thousand range.

In cases where irradiation is to be carried out with electron beams and x-rays at dose rates according to the invention, it is possible to carry out the method step according to the invention one after the other, in any desired order, with electron beams and x-rays. In a further embodiment, it is possible to use a device for the production of electron beams which, in addition to electron beams, also emits x-rays at dose rates according to the invention.

Within the meaning of the cells discussed here, a mammalian cell is "viable" if the cell can be determined to be viable by means of a method for determining viability described in the prior art. Such methods are well known in the prior art and include diffusion-based methods and methods based on the measurement of electrical resistance. In a preferred embodiment, a diffusion-based method on a perforated cell membrane is used for determining viability. Diffusion-based methods on a perforated cell membrane are well known in the prior art and include the use of perforation dyes such as trypan blue, brilliant blue FCF, crystal violet, and the DNA-intercalating fluorescent dyes 4',6-diamidine-2-phenylindol (DAPI), ethidium bromide, or propidium iodide. These perforation dyes can penetrate through perforated cell membranes into limited-viability cells. Living cells, in contrast, show virtually no staining. Counting of the viable cells after staining can be carried out for example microscopically, by trypan blue staining, and/or by propidium iodide staining using flow cytometry, and can be carried out manually or by a camera- and/or computer-supported method. In a particularly preferred embodiment, the viability of mammalian cells is determined by trypan blue staining, as described in the examples.

Viable cells whose proliferation capacity is reduced, in particular reduced by 100%, will die after a certain period of time. For this reason, the presence of a viable cell after irradiation is preferably determined within 1 d to 7 d after irradiation, in particular 2 d or 3 d to 7 d after irradiation. For example, the viability can be determined 2 d, 3 d, 4 d, 5 d, 6 d, or 7 d after irradiation.

In a preferred embodiment of the present invention, at least 10%, 20%, 30%, 40%, 50%, 60%, 70% or 80% of the irradiated target mammalian cells are viable 1 d, 2 d, 3 d, 4 d, 5 d, 6 d, or 7 d after irradiation, and more preferably, at least 10%, 20%, 30%, 40%, 50%, 60%, 70%, or 80% of the irradiated target mammalian cells are viable 3 d after irradiation.

In a further preferred embodiment, a method according to the invention is characterized in that the population of mammalian cells or the target mammalian cells is/are suitable for administration to an individual and/or is/are suitable for producing a cellular agent for administration to an individual after irradiation.

In a further preferred embodiment, a method according to the invention is characterized in that the population of mammalian cells or the target mammalian cells is/are suitable for therapeutic, preventive or cosmetic administration to an individual and/or is/are suitable for producing a cellular therapeutic, preventive or cosmetic agent for administration to an individual.

In particular, the target mammalian cells are reduced in their proliferation capacity, and the viability is maintained for 1 d, 2 d, 3 d, 4 d, 5 d, 6 d, or 7 d after irradiation in at least 10%, 20%, 30%, 40%, 50%, 60%, 700, or 80% of the target mammalian cells.

Depending on the type of the population of mammalian cells and the target mammalian cells, the cells are suitable and provided for therapeutic, preventive, and/or cosmetic administration to an individual.

In the case of vaccines, for example in the area of a hyperproliferative disease or cancer, the cells are suitable for therapeutic and/or preventive administration to an individual for use in the prevention or treatment of cancer or a hyperproliferative disease.

In the case of transplants, such as hematopoietic stem cell preparations, the cells are suitable for therapeutic administration to an individual for use in the prevention or treatment of a disease requiring transplantation, such as leukemia in the case of hematopoietic stem cell preparations.

In the case of immune cells, the cells are suitable for therapeutic and/or preventive administration to an individual for use in the prevention or treatment of e.g. a hyperproliferative disease, cancer, immune disease or chronic degenerative disease, depending on the immune cells.

In a particularly preferred embodiment, the population of mammalian cells or the target mammalian cells is/are suitable for administration to an individual for the treatment and/or prevention of a hyperproliferative disease, immune disease, or chronic degenerative disease, and/or the agent comprising at least one treated viable target mammalian cell is a transplant, in particular a hematopoietic stem cell transplant, a vaccine, a cytotoxic agent, or an apheresis product.

In a further preferred embodiment, a method according to the invention is characterized in that the dose is in the range of 0.1 Gy to 1 kGy, preferably in the range of 1 Gy to 100 Gy.

In particular, a method according to the invention is characterized in that the dose is in the range of 0.5 Gy to 800 Gy, preferably in the range of 1 Gy to 5 Gy, 10 Gy, 20 Gy, 30 Gy, 40 Gy, 50 Gy, 60 Gy, 70 Gy, 80 Gy, 90 Gy, 100 Gy, 200 Gy, 300 Gy, 400 Gy, 500 Gy, 600 Gy, 700 Gy, 800 Gy, 900 Gy, or 1 kGy. In a further preferred embodiment, the dose is in the range of 1 Gy to 5 Gy, 1 Gy to 10 Gy, 1 Gy to 20 Gy, 1 Gy to 30 Gy, 1 Gy to 40 Gy, 1 Gy to 50 Gy, 1 Gy to 60 Gy, 1 Gy to 70 Gy, 1 Gy to 80 Gy, 1 Gy to 90 Gy, 1 Gy to 100 Gy, or 1 Gy to 200 Gy. In a further more preferred embodiment, the dose is in the range of 5 Gy to 10 Gy, 5 Gy to 20 Gy, 5 Gy to 30 Gy, 5 Gy to 40 Gy, 5 Gy to 50 Gy, 5 Gy to 60 Gy, 5 Gy to 70 Gy, 5 Gy to 80 Gy, 5 Gy to 90 Gy, 5 Gy to 100 Gy, or 5 Gy to 200 Gy. In a further more preferred embodiment, the dose is in the range of 10 Gy to 20 Gy, 10 Gy to 30 Gy, 10 Gy to 40 Gy, 10 Gy to 50 Gy, 10 Gy to 60 Gy, 10 Gy to 70 Gy, 10 Gy to 80 Gy, 10 Gy to 90 Gy, 10 Gy to 100 Gy, or 10 Gy to 200 Gy. For example, the dose can be in the range of 10 Gy to 30 Gy.

In a further preferred embodiment, a method according to the invention is characterized in that the dose rate is in the range of 10 Gy/sec to $10^4$ Gy/sec, in particular 50 Gy/sec to $10^3$ Gy/sec, for example 10 Gy/sec to $10^3$ Gy/sec or 50 Gy/sec to $10^3$ Gy/sec.

As mentioned above, a shorter dose application time is advantageous.

In a further preferred embodiment, a method according to the invention is therefore characterized in that the irradiation time is in the range of 0.1 msec to 10 sec, more preferably wherein the irradiation time is in the range of 10 msec to 8 sec. More preferably, the irradiation time is in the range of 0.1 msec to 1, 2, 3, 4, 5, 6, 7, 8, 9, or 10 sec, or 0.5 msec to 1, 2, 3, 4, 5, 6, 7, 8, 9, or 10 sec.

In a further preferred embodiment, a method according to the invention is characterized in that the composition comprising a population of mammalian cells is in the form of a thin layer in the irradiation of step (i).

A composition is in the form of a thin layer if the composition is thin with respect to the penetration depth of the radiation during irradiation, in particular wherein the length of the beam path through the composition during irradiation is less than 5 cm.

The irradiation of the composition as a thin layer allows essentially homogeneous irradiation of the mammalian cells in the composition.

During irradiation, the composition as a thin layer can for example be on a solid carrier, be in the form of a thin liquid stream, or be in the form of an aerosol, such as aerosol particles.

In a preferred embodiment, the composition is on a solid carrier during irradiation. The solid carrier preferably comprises a planar or essentially planar surface to which the composition is applied. For example, the solid carrier may be a planar or essentially planar surface or may comprise cavities that contain a planar or essentially planar surface. The solid carrier may be flexible, such as a film, or inflexible, such as a plate or array.

The solid carrier can be any carrier that is compatible, essentially non-toxic, and preferably essentially radiation compatible with respect to the desired population of mammalian cells and target mammalian cells. A carrier is radiation compatible if no migration of harmful radiolysis products from the irradiated carrier into the composition takes place on irradiation. Suitable examples include plastic films such as polypropylene, PE, or PVC films, plastic plates and arrays such as culture plates with one or a plurality of wells, or plastic dishes such as petri dishes.

In a preferred form, the composition is irradiated on a solid carrier such that the rays first strike the composition and then the solid carrier.

There are no particular limitations on the size and shape of the surface of the irradiated composition. Preferably, the surface of the irradiated composition should be configured such that it is possible to homogeneously irradiate the entire composition. This can be carried out by irradiation with the composition kept in a stationary position or by continuously feeding the composition through the beam path. For example, the surface area of the composition in step (i) can be between 1 mm$^2$ and 100 cm$^2$.

During irradiation, the composition can comprise a cover or no cover. A cover can for example be a lid or a film. For example, the composition can be in a bag. If a cover is used, the cover should preferably be permeable to radiation and radiation-resistant.

In order to achieve essentially homogeneous irradiation, the thin layer is preferably configured such that the thickness of the layer in the preferred direction of propagation of the beam path corresponds to the diameter of one or a few mammalian cell(s), for example the diameter of 1, 2, 3, 4, 5, 6, 7, 8, 9, 10, 50, 100, or 1000 mammalian cell(s). If a composition is to be irradiated as a thin layer on a solid carrier, as in the examples, the rays preferably strike the layer perpendicularly or essentially perpendicularly. In the embodiment of a thin liquid stream, the thin liquid stream is preferably irradiated laterally, essentially perpendicularly to the liquid stream.

In a particularly preferred embodiment, the thin layer therefore has a thickness of between 0.5 μm and 3 cm. Preferably, the thin layer therefore has a thickness of between 1 μm and 1 or 2 cm, 1 μm and 100 μm, or 1 μm and 50 μm.

Prior to irradiation, the composition comprising a population of mammalian cells can be any desired composition that contains mammalian cells comprising at least one living or viable target mammalian cell. For example, the composition can be frozen, freeze-dried, a gel, a sol, or a liquid. Preferably, the composition is a gel, in particular a hydrogel, or a liquid.

In a further preferred embodiment, the composition comprising a population of mammalian cells, in the irradiation of step (i), is frozen, a gel, a sol, or a liquid, preferably a gel or a liquid. In the case of a liquid composition, the mammalian cells may be present as a suspension and/or adhere to a solid carrier.

The composition preferably comprises water, more preferably an aqueous solution, wherein the aqueous solution particularly preferably contains one or a plurality of buffer substances and/or medium. The aqueous buffered solution can for example be PBS. The pH of such a solution is preferably in the range of 5.5 to 8.5, more preferably in the range of 6.5 to 8.0. The composition can further contain hydrogel-forming substances, or can be frozen or liquid.

In a further preferred embodiment, a method according to the invention is therefore characterized in that the composition comprising a population of mammalian cells, in the irradiation of step (i), (a) is in the form of a cell suspension, or
(b) is in the form of an adherent cell layer on a solid carrier.

The adherent cell layer can preferably comprise one or a plurality of, for example 1, 2, 3, 4, 5, 6, 7, 8, 9, 10, or 50, cell layers.

In a further preferred embodiment, the population of mammalian cells, in the irradiation of step (i), contains essentially no tissue, more preferably no contiguous tissue, such as sections of the liver. Even distribution of the cells is advantageous for homogeneous irradiation.

The electron beams can preferably be accelerated with energies in the range of 80 keV to 10 MeV.

In a further preferred embodiment, a method according to the invention is characterized in that irradiation is carried out with electron beams and the electron beams are accelerated with an acceleration energy of between 80 keV and 10 MeV, in particular with an acceleration energy of between 80 keV and 300 keV.

For example, the electron beams can be accelerated with an acceleration energy of between 80 keV and 1 MeV, 80 keV and 250 keV, 300 keV, 400 keV, 500 KeV, 600 KeV, or 700 keV.

In a further preferred embodiment, a method according to the invention is characterized in that irradiation is carried out with x-rays and the x-ray radiation has an energy of between 5 keV and 600 keV, preferably between 5 keV and 300 keV, 400 keV, or 500 keV, and more preferably between 10 and 200 keV.

In a preferred embodiment, the electron beams and/or x-rays are essentially applied under a standard pressure atmosphere, wherein the standard pressure atmosphere is preferably an atmospheric gas mixture.

An increase in temperature can occur during irradiation. In order to prevent denaturing processes, it is therefore advantageous if the temperature increases only slightly or not at all.

In a further preferred embodiment of the method according to the invention, the temperature of the composition before irradiation is therefore between −200° C. and 38° C., preferably between −130° C., −80° C., −10° C., or 0° C. and 37.7° C., more preferably between 10° C. and 37.5° C., even more preferably between 15° C. and 37.5° C.

In another embodiment, it is possible to carry out irradiation with temperatures of the composition prior to irradiation of less than 1° C., for example with frozen compositions. In this case, the composition can also have a temperature of less than 1° C. after irradiation, or the temperature of the composition after irradiation can be 1° C. or higher.

In a further preferred embodiment of the method according to the invention, the increase in temperature of the composition after irradiation compared to before irradiation is between 0 K and 5 K, preferably between 0 K and 1 K.

In a further preferred embodiment of the method according to the invention, the temperature of the composition after irradiation is therefore between −200° C. and 38° C., preferably between −130° C., −80° C., −10° C., or 0° C. and 37.7° C., more preferably between 10° C. and 37.5° C., and even more preferably between 15° C. and 37.5° C.

In a further preferred embodiment of the method according to the invention, the density of the composition is between 0.9 and 2 g/cm$^3$, preferably between 1.0 and 1.8 g/cm$^3$.

By means of the irradiation of mammalian cells according to the invention, the viability of the cells is maintained, i.e. largely maintained, for 1 d, 2 d, 3 d, 4 d, 5 d, 6 d, or 7 d after irradiation in at least 10%, 20%, 30%, 40%, 50%, 60%, 70%, or 80% of the cells of the population, while the proliferation capacity is reduced.

In a preferred embodiment, the viability of the cells is maintained for 3 d after irradiation in at least 10%, 20%, 30%, 40%, 50%, 60%, 70%, or 80% of the cells of the population. The person skilled in the art knows that different cells can show different sensitivity to radiation, and that the values can therefore vary for different cells.

In a preferred embodiment, after irradiation, the composition comprising a population of mammalian cells comprises at least one viable target mammalian cell, and the target mammalian cell(s) of the composition show(s) reduced proliferation capacity after irradiation. Preferably, the proliferation capacity can be reduced by at least 20%, 30%, 40%, 50%, 60%, 70%, 80%, 90%, or 95%.

In a preferred embodiment, the proliferation capacity after irradiation is reduced by 100%. In this embodiment, these cells can no longer proliferate. A reduction in proliferation capacity by 100% may be necessary in the case of hyperproliferative cells, for example the tumor cells or immortalized cell lines to be administered, as these cells are not suitable for administration to an individual while they still have proliferation capacity.

The proliferation capacity can be determined by determining the cell count under conditions that allow the growth thereof in vitro. Such conditions are ordinarily 10° C. to 38° C., in the presence of a suitable culture medium. The cell count is determined at at least two different times. Methods for determining the cell count are well known to the person skilled in the art and include for example methods for determining the proliferation or viability of cells. Determination of viability can be carried out as described above. Methods for determining proliferation are also well known to the person skilled in the art and include for example the above-mentioned viability tests, as well as the chromium release assay or the lymphocyte transformation test (LTT).

The reduction in proliferation capacity after irradiation is understood to be a reduction in proliferation capacity compared to the same mammalian cells not subjected to irradiation, with all the other conditions being the same.

In a preferred embodiment, the irradiated, viable target mammalian cells show a desired biological activity, in particular 1 d, 2 d, 3 d, 4 d, 5 d, 6 d, or 7 d after irradiation. This desired biological activity depends on the type of target mammalian cell. For example, the cell can show a therapeutic, preventive, or cosmetic activity. Preferably, the biological activity can be cytotoxicity, immunogenicity, immunosuppression, or induction of immune tolerance. In the case of NK cells, the biological activity is preferably cytotoxicity with respect to tumor cells. NK cells were successfully irradiated by the method according to the invention, as shown in the examples and FIGS. 2 to 12. Preferably, the desired biological activity 1 d, 2 d, 3 d, 4 d, 5 d, 6 d, or 7 d after irradiation is at least 10%, 20%, 30%, 40%, 50%, 60%, 70%, 80%, or 90% of the biological activity of the same mammalian cells not subjected to irradiation, with all of the other conditions being the same. More preferably, the desired biological activity 3 d after irradiation is at least 10%, 20%, 30%, 40%, 50%, 60%, 70%, 80%, or 90% of the biological activity of the same mammalian cells not subjected to irradiation, with all of the other conditions being the same. Methods for determining the desired biological activity are well known to the person skilled in the art. For example, in vitro and/or in vivo tests for determining cytotoxicity, immunogenicity, immunosuppression or the induction of immune tolerance are well known.

In a further preferred embodiment, a method according to the invention is characterized in that (a) the composition comprising a population of mammalian cells comprises at least one viable target mammalian cell after irradiation, and (b) the target mammalian cell(s) of the composition show reduced proliferation capacity after irradiation, in particular wherein the target mammalian cell(s) is/are (a) hyperproliferative or immortalized cell(s) and the proliferation capacity after irradiation is reduced by 100%, and, optionally, (c) the target mammalian cell(s) of the composition show(s) biological activity after irradiation, in particular therapeutic, preventive, or cosmetic activity, preferably wherein the biological activity is selected from the group composed of cytotoxicity, immunogenicity, immunosuppression, and inducing immune tolerance.

In a further embodiment, the present invention relates to a method for producing an agent, comprising at least one treated viable target mammalian cell that is suitable for administration to an individual, characterized in that:

(a0) a composition comprising a population of mammalian cells, wherein the population of mammalian cells contains at least one target mammalian cell, is prepared, (a1) the a method according to the invention is carried out, (a2) optionally, one or a plurality of pharmaceutically acceptable carriers and/or auxiliaries are added to the composition comprising a population of mammalian cells, and/or (a3) optionally, one or a plurality of further agents having a therapeutic, preventive, or cosmetic action are added to the composition comprising a population of mammalian cells, wherein steps (a1) to (a3) are carried out in any desired order.

Using the method according to the invention, it is therefore possible to irradiate an otherwise finished composition for administration, for example a vaccine, a cytotoxic product, or an apheresis product, that already contains suitable auxiliaries and/or adjuvants and/or one or a plurality of further agents having a therapeutic, preventive, or cosmetic action.

In another embodiment, irradiation of the population can be carried out according to the invention, and one or a plurality of pharmaceutically acceptable carriers and/or auxiliaries can then optionally be added to the composition, and/or one or a plurality of further agents having a therapeutic, preventive, or cosmetic action can optionally be added to the composition.

In a further preferred embodiment of the method according to the invention, the composition in step (i) is therefore a liquid suspension, a gel, or adherent cells on a solid carrier, or a frozen composition containing water, such as a suspension of the mammalian cells in an aqueous solution, wherein the aqueous solution particularly preferably contains one or a plurality of buffer substances and/or medium. For example, the aqueous buffered solution can be PBS. The pH of such a solution is preferably in the range of 5.5 to 8.5, more preferably in the range of 6.5 to 8.0. Furthermore, in step (i), the composition can comprise one or a plurality of further pharmaceutically acceptable carriers and/or auxiliaries, or if desired, these may be added after step (i) and optionally step (ii). Furthermore, one or a plurality of further agents having a therapeutic, preventive, or cosmetic action may be added to the composition in step (i), or if desired, these may be added after step (i) and optionally step (ii).

In a further embodiment of the method according to the invention, in step (i), the composition therefore contains pharmaceutically acceptable carriers and/or auxiliaries.

In the case of vaccines, adjuvants can be contained as auxiliaries. Adjuvants are well known to the person skilled in the art. Suitable adjuvants are those that are sufficient to enhance an immune response to an immunogen. Suitable adjuvants for antibody-based vaccines are for example aluminum salts such as aluminum phosphate or aluminum hydroxide, squalene mixtures (SAF-1), muramyl peptide, saponin derivatives, mycobacterial cell wall preparations, monophosphoryl lipid A, mycolic acid derivatives, nonionic block copolymers, surfactants, Quil A, cholera toxin B subunit, polyphosphazenes and derivatives and immune stimulating complexes (ISCOMs), such as those described in Takahashi et al. (1990) Nature 344:873-875. An example of a suitable adjuvant for Th-1-based cytotoxic vaccines is poly I:C.

Suitable carriers and auxiliaries are for example water or an aqueous solution suitable for administration, which particularly preferably contains one or a plurality of buffer substances. Suitable carriers and auxiliaries can be selected independently of the type of administration, the dose, the administration form, storage, and the active ingredient(s). Adjuvants include carrier materials such as microcrystalline cellulose, lactose, mannitol, solvents such as polyethylene glycols, emulsifiers and dispersants or wetting agents, for example sodium dodecyl sulfate, polyoxysorbitan oleate, binders such as polyvinylpyrrolidone, synthetic and natural polymers such as albumin, stabilizers, for example antioxidants such as ascorbic acid, dyes, for example inorganic pigments such as iron oxides, and flavor and/or odor correctants.

The dose and administration route also depend on the type of cellular agent to be administered. Suitable routes include systemic administration, such as intravenous or intraperitoneal administration, enteral or parenteral administration, or local administration, such as intratumoral or subcutaneous administration. Moreover, for example, depending on the type of cellular agent to be administered, $10^4$ to $10^9$ cells per administration can be administered to an individual.

It may be necessary to deviate from the above-mentioned amounts, specifically depending on body weight, administration route, individual reaction to the active ingredient, type of preparation, and the time or interval at which administration takes place. In some cases, it may be sufficient to use less than the minimum amount, while in other cases, the above-mentioned upper limit must be exceeded. In the case of administration of large amounts, it may be advisable to divide these into multiple individual administrations throughout the day.

In a further embodiment, the present invention relates to an agent comprising at least one treated viable target mammalian cell that is suitable for administration to an individual and/or treated viable target mammalian cell that is suitable for producing a cellular agent for administration to an individual, producible by any of the above-described methods according to the invention.

In a preferred embodiment, the agent according to the invention and/or the treated viable target mammalian cell according to the invention is/are characterized by having one or a plurality of features that is/are disclosed for the method according to the invention, preferably wherein the agent is for use in the treatment or prevention of a disease.

In a further embodiment, the present invention relates to the use of a device for the production of electron beams and/or x-rays (i) for producing an agent comprising at least one treated viable target mammalian cell that is suitable for administration to an individual and/or for producing treated viable target mammalian cells that are suitable for producing a cellular agent for administration to an individual, and/or (ii) for irradiating a population of mammalian cells comprising at least one target mammalian cell with electron beams and/or x-rays, characterized in that a composition comprising a population of mammalian cells is irradiated in vitro with electron beams and/or x-rays, wherein the population of mammalian cells contains at least one target mammalian cell, and wherein the dose rate is in the range of 5 Gy/sec to $10^7$ Gy/sec.

In a further embodiment, the present invention relates to the use of electron beams and/or x-rays (i) for producing an agent comprising at least one treated viable target mammalian cell that is suitable for administration to an individual and/or for producing treated viable target mammalian cells that are suitable for producing a cellular agent for administration to an individual, and/or (ii) for irradiating a population of mammalian cells comprising at least one target mammalian cell with electron beams and/or x-rays, characterized in that a composition comprising a population of mammalian cells is irradiated in vitro with electron beams and/or x-rays, wherein the population of mammalian cells contains at least one target mammalian cell, and wherein the dose rate is in the range of 5 Gy/sec to $10^7$ Gy/sec.

For the uses of the present invention, the same embodiments that are also disclosed for the methods according to the invention are applicable. In a further preferred embodiment, a use according to the invention is therefore characterized in that it shows one or a plurality of features that is/are disclosed for the method according to the invention.

FIGURES

FIG. 1: Loss of anti-tumor cytotoxicity of conventionally (gamma, 10 Gy) irradiated NK cell lines according to Tam et al. (1999) and Suck et al. (2006). "cont."=control. NK-92 and KHYG-1=NK cell lines. K562=lymphoma tumor cell line as a cytotoxic target. A): NK-92-NK cell line; B): KHYG-1 NK cell line. Left bars respectively: control; right bars respectively: 3 days after irradiation with 10 kGy.

Figure 2:
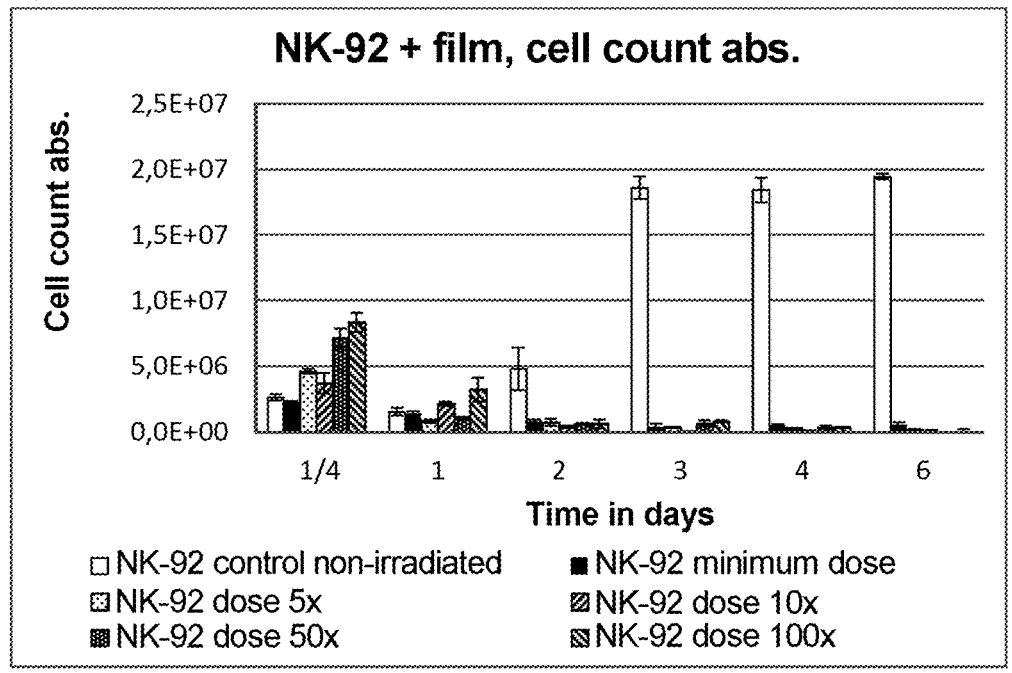
Figure 2:
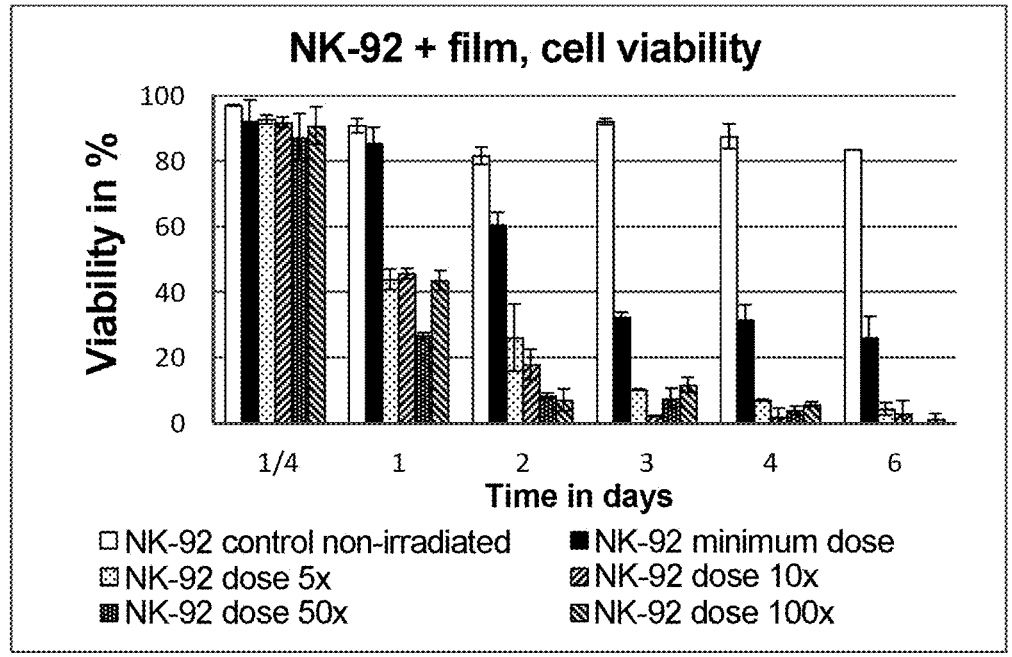

FIG. 2: Irradiation of NK-92 cells with various doses using an electron beam irradiator and limitation of proliferation and maintenance of viability of irradiated cells. The control was treated in the same manner, except that irradiation was simulated. Bars from left respectively: 1. Untreated NK-92 cells; 2. NK-92 cells treated with a dose of 20±10 Gy (referred to in the following as the minimum dose); 3. NK-92 cells treated with 5× the minimum dose; 4. NK-92 cells treated with 10× the minimum dose; 5. NK-92 cells treated with 50× the minimum dose; 6. NK-92 cells treated with 100× the minimum dose. Electron irradiation of a thin liquid film of a cell suspension limits the proliferation activity of the cellular component while largely maintaining viability.

Figure 3:
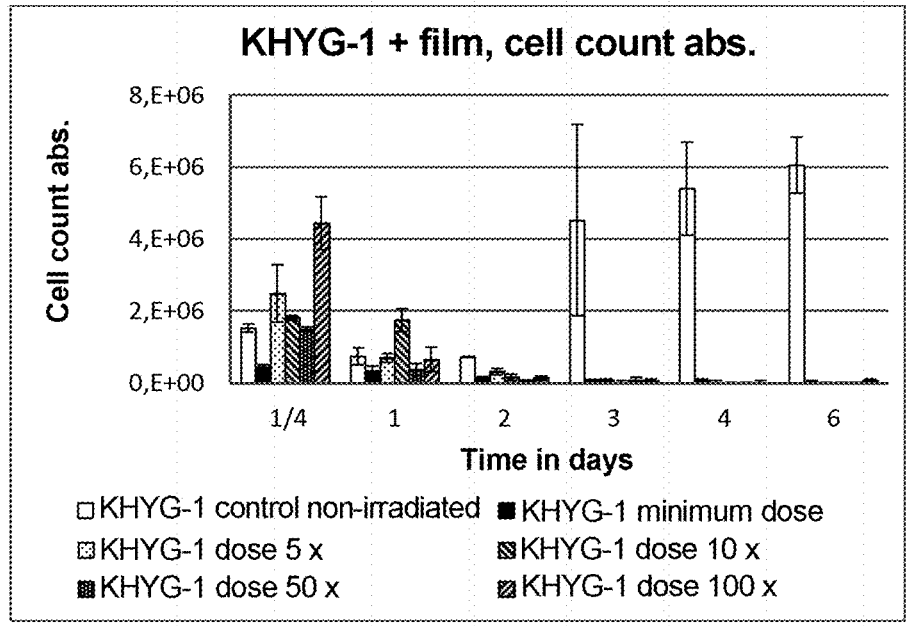
Figure 3:
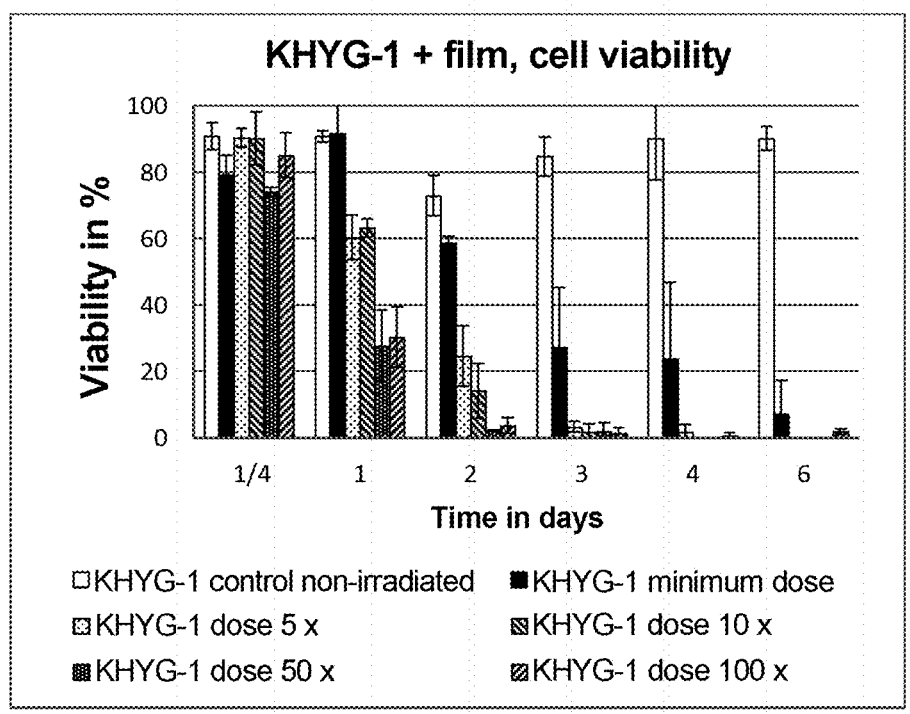

FIG. 3: Irradiation of KHYG-1 NK cells using an electron beam irradiator and limitation of proliferation and maintenance of viability of irradiated cells. The control was treated in the same manner, except that irradiation was simulated. Bars from left respectively: 1. Untreated KHYG-1 cells; 2. KHYG-1 cells treated with the minimum dose; 3. KHYG-1 cells treated with 5× the minimum dose; 4. KHYG-1 cells treated with 10× the minimum dose; 5. KHYG-1 cells treated with 50× the minimum dose; 6. KHYG-1 cells treated with 100× the minimum dose. Electron irradiation of a thin liquid film of a cell suspension limits the proliferation activity of the cellular component while largely maintaining viability.

Figure 4:
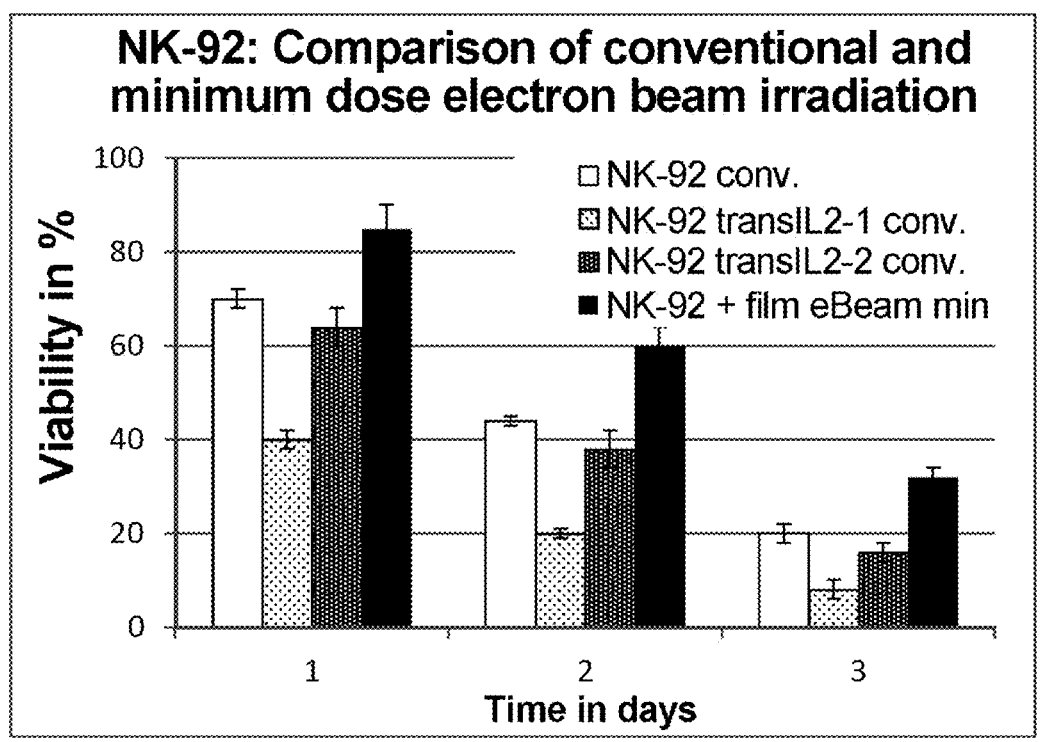
Figure 4:
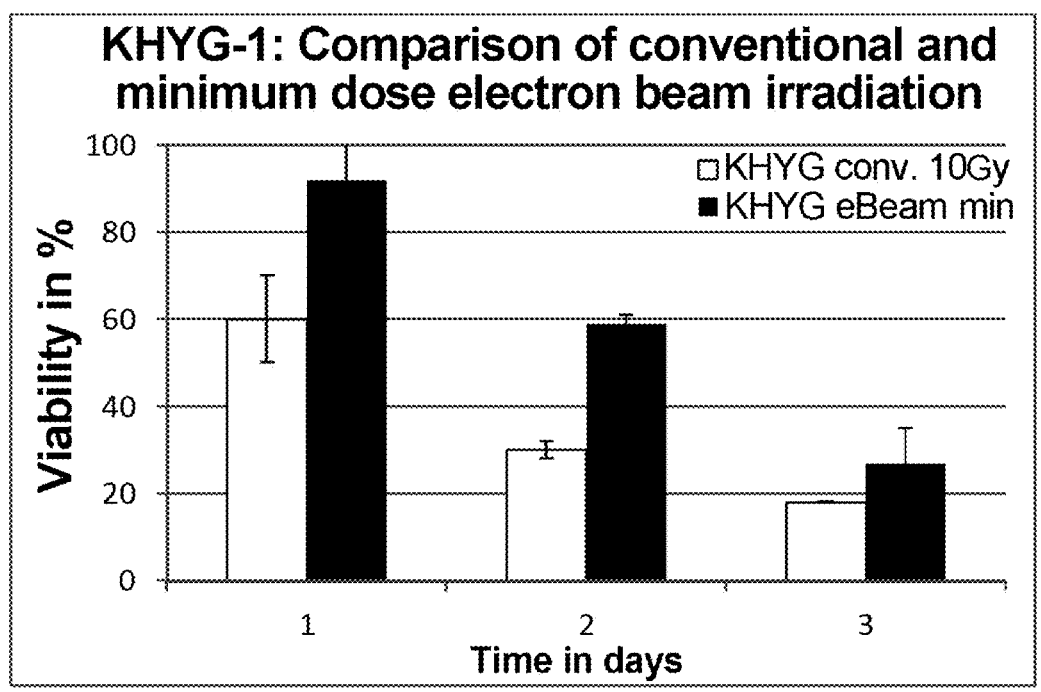

FIG. 4: Comparison of published results for viabilities of NK-92 or KHYG-1 NK cell lines that were conventionally irradiated (gamma irradiation, 10 Gy, modified according to Tam et al. 1999 for NK-92 and Suck et al. 2006 for KHYG-1) and irradiated with electron beams in order to minimally inhibit proliferation. A: Bars from left respectively: 1. conventionally treated NK-92 cells (10 Gy gamma); 2. conventionally treated NK-92 cells transIL2-1; 3. conventionally treated NK-92 cells transIL2-1; 4. NK-92 cells treated with minimum dose electron beams. B: Bars from left respectively: 1. conventionally treated KHYG-1 cells (10 Gy gamma); 2. KHYG-1 cells treated with minimum dose electron beams.

Figure 5:
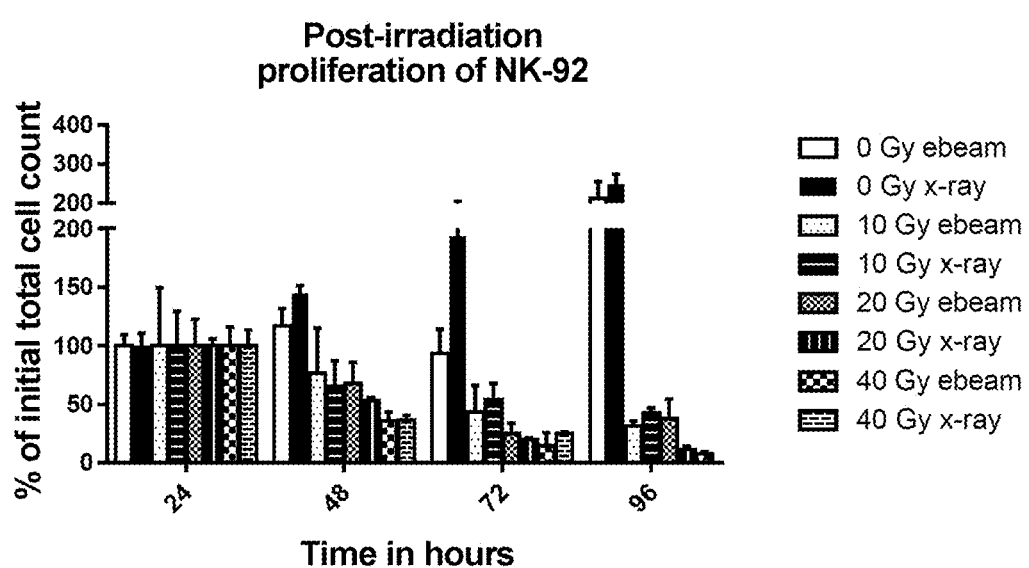

FIG. 5: Proliferation of NK92 after conventional irradiation or minimum-dose electron beam irradiation. The NK cell line NK92 was irradiated with conventional x-ray irradiation (doses: 10, 20 and 40 Gy; device: SARRP, Xstrahl Limited, UK) ("x-ray") or minimum-dose electron beam irradiation ("ebeam"). Electron irradiation was carried out under the following conditions: dose rate: approx. 300 Gy/sec (calculated), irradiation time: between 0.033 and 6.6 sec., calculated doses: 0, 10, 20, and 40 Gy. The cells were seeded immediately after irradiation at a density of 1 mill. cells/ml onto NK cell medium in a 6-well plate with a flat bottom. The cells were counted by trypan blue staining. Proliferation was observed over four days (24, 48, 72, and 96 hours). The count after 24 hours of irradiation was taken as a reference value. The conventional irradiation data were calculated from an experiment with triplicates and were expressed as mean value ±SEM. The data for minimum-dose electron beam irradiation were calculated from three independent experiments and were expressed as mean value ±SEM, n=3.

Figure 6:
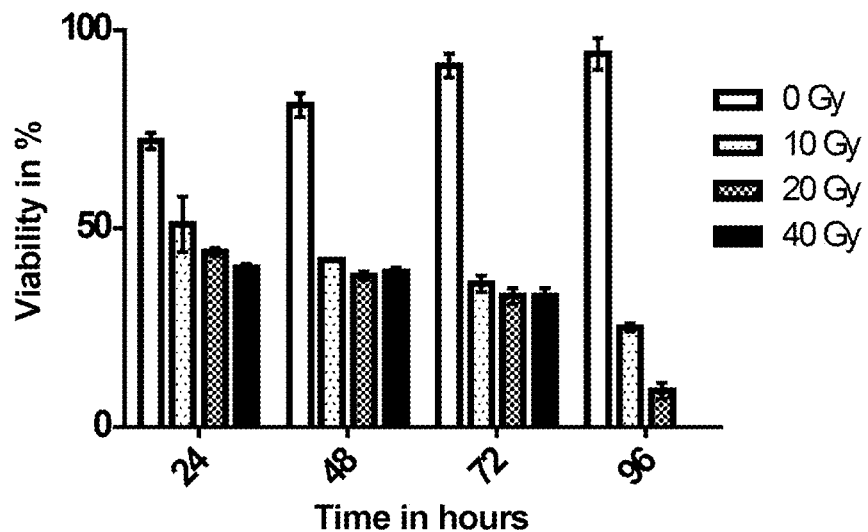
Figure 6:
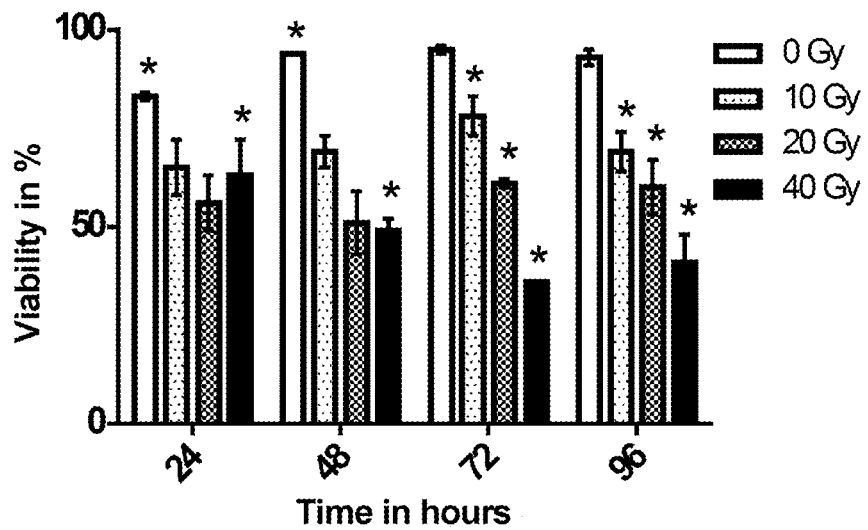

FIG. 6: Viability of NK92 after conventional irradiation or minimum-dose electron beam irradiation. The NK cell line NK92 was irradiated with (a) conventional x-ray irradiation (doses: 10, 20, and 40 Gy; device: SARRP, Xstrahl Limited, UK) or (b) minimum-dose electron beam irradiation. Electron irradiation was carried out under the following conditions: dose rate: approx. 300 Gy/sec (calculated), irradiation time: between 0.033 and 6.6 sec., calculated doses: 0, 10, 20, and 40 Gy. The cells were seeded at a density of 1 mill. cells/ml onto NK cell medium in a 6-well plate with a flat bottom. Cell viability was measured using the BD Accuri™ C6. Viability was observed over four days (24, 48, 72, and 96 hours). The conventional irradiation data were calculated from an experiment with duplicates and were expressed as mean value ±SD. The data for minimum-dose electron beam irradiation were calculated from three independent experiments and were expressed as mean value ±SD, n=3. Compared to the conventional irradiation data, statistical significance was reached at $p<0.05$ (*) and calculated by the unpaired two-sample t-test.

Figure 7:
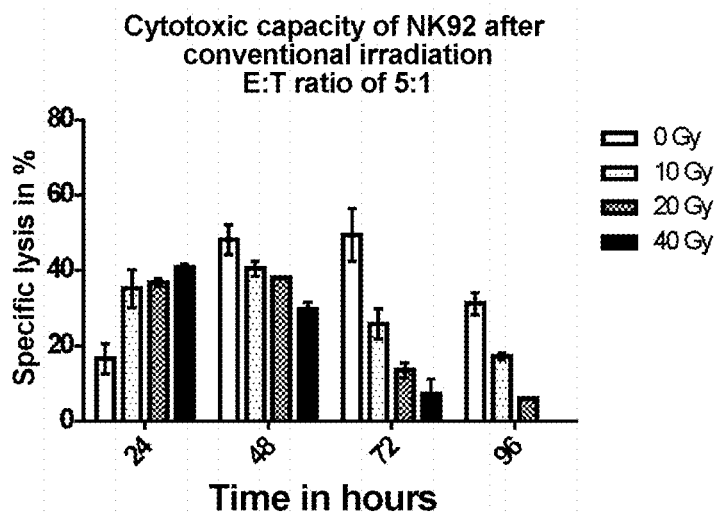
Figure 7:
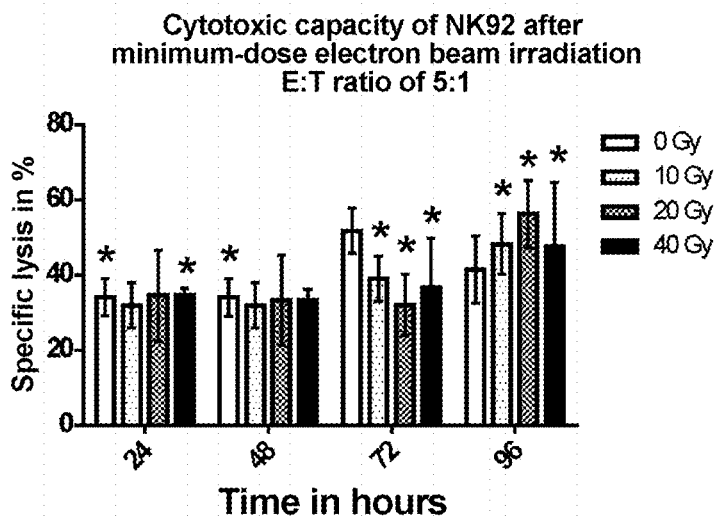

FIG. 7: Cytotoxic capacity of NK92 after conventional irradiation and minimum-dose electron beam irradiation. Ratio of effector cells to target cells 5:1. The NK cell line NK92 was irradiated with (a) conventional x-ray irradiation (doses: 10, 20, and 40 Gy; device: SARRP, Xstrahl Limited, UK) or (b) minimum-dose electron beam irradiation. Electron irradiation was carried out under the following conditions: dose rate: approx. 300 Gy/sec (calculated), irradiation time: between 0.033 and 6.6 sec. (calculated doses: 0, 10, 20, and 40 Gy), and specific lysis was detected over four days (24, 48, 72, and 96 hours). For the europium cytotoxicity assay, NK92 was co-cultivated for two hours with the target cell line K562 at an E:T ratio of 5:1 in NK cell medium. The conventional irradiation data were calculated from an experiment with duplicates and were expressed as mean value ±SD. The data for minimum-dose electron beam irradiation were calculated from three independent experiments with triplicates and were expressed as mean value ±SD. Compared to the conventional irradiation data, statistical significance was reached at $p<0.05$ (*) and calculated by the unpaired two-sample t-test. Abbreviation: E:T: effector cells to target cells.

Figure 8:
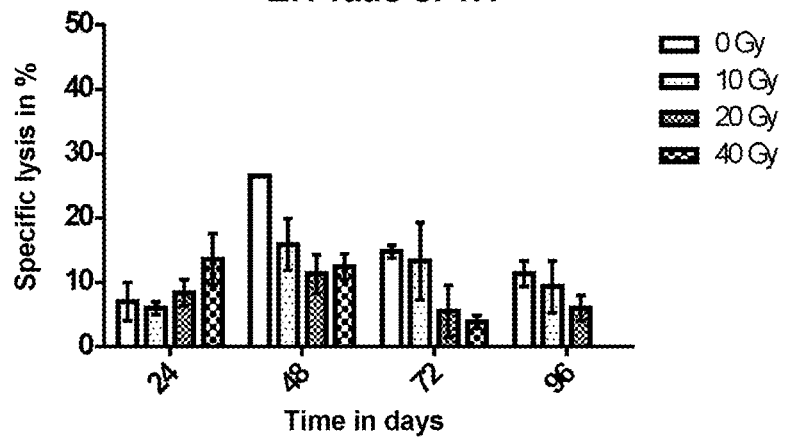
Figure 8:
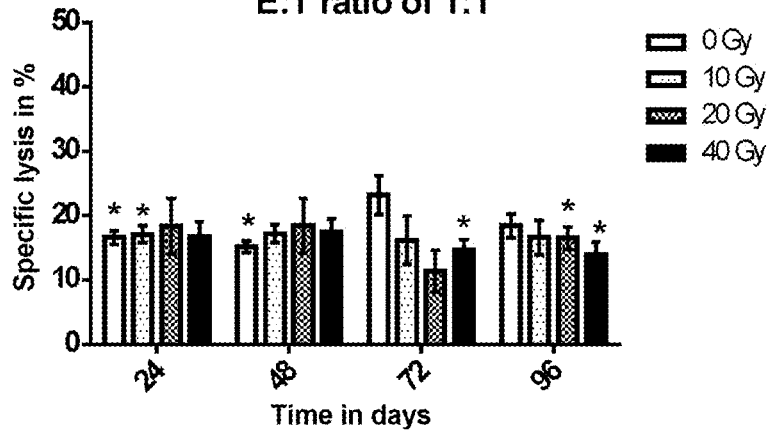

FIG. 8: Cytotoxic capacity of NK92 after conventional irradiation and minimum-dose electron beam irradiation. Ratio of effector cells to target cells 1:1. The NK cell line NK92 was irradiated with (a) conventional x-ray irradiation (doses: 10, 20, and 40 Gy; device: SARRP, Xstrahl Limited, UK) or (b) minimum-dose electron beam irradiation. Electron irradiation was carried out under the following conditions: dose rate: approx. 300 Gy/sec (calculated), irradiation time: between 0.033 and 6.6 sec. Calculated doses: 0, 10, 20, and 40 Gy. Specific lysis was determined over four days (24, 48, 72, and 96 hours). For the europium cytotoxicity assay, NK92 was co-cultivated for two hours with the target cell line K562 at an E:T ratio of 1:1 in NK cell medium. The conventional irradiation data were calculated from an experiment with duplicates and were expressed as mean value ±SD. The data for minimum-dose electron beam irradiation were calculated from three independent experiments with triplicates and were expressed as mean value ±SD. Compared to the conventional irradiation data, statistical significance was reached at $p<0.05$ (*) and calculated by the unpaired two-sample t-test. Abbreviation: E:T: effector cells to target cells.

Figure 9:
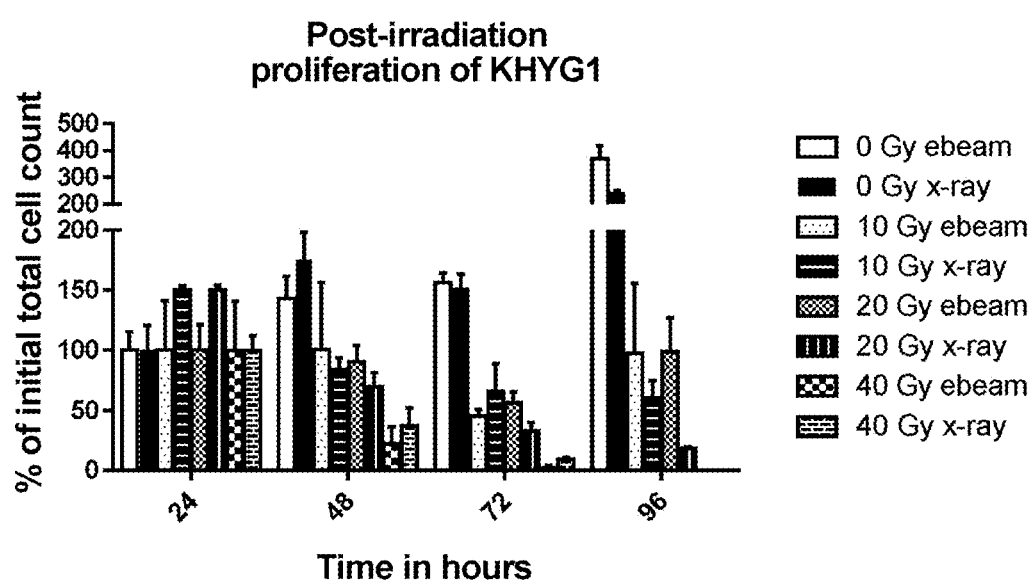

FIG. 9: Proliferation of KHYG1 after conventional irradiation or minimum-dose electron beam irradiation. The NK cell line KHYG1 was irradiated with conventional x-ray irradiation (x-ray radiation (doses: 10, 20, and 40 Gy; device: SARRP, Xstrahl Limited, UK) device: SARRP, Xstrahl Limited, UK ("x-ray") or minimum-dose electron beam irradiation (ebeam). Electron irradiation was carried out under the following conditions: dose rate: approx. 300 Gy/sec., calculated doses: 0, 10, 20, and 40 Gy. The cells were seeded immediately after irradiation at a density of 1 mill. cells/ml onto NK cell medium in a 6-well plate with a flat bottom. The cells were counted by trypan blue staining. Proliferation was observed over four days (24, 48, 72, and 96 hours). The count after 24 hours of irradiation was taken as a reference value. The conventional irradiation data were calculated from an experiment with triplicates and were expressed as mean value ±SEM. The data for minimum-dose electron beam irradiation were calculated from three independent experiments and were expressed as mean value ±SEM, n=3.

Figure 10:
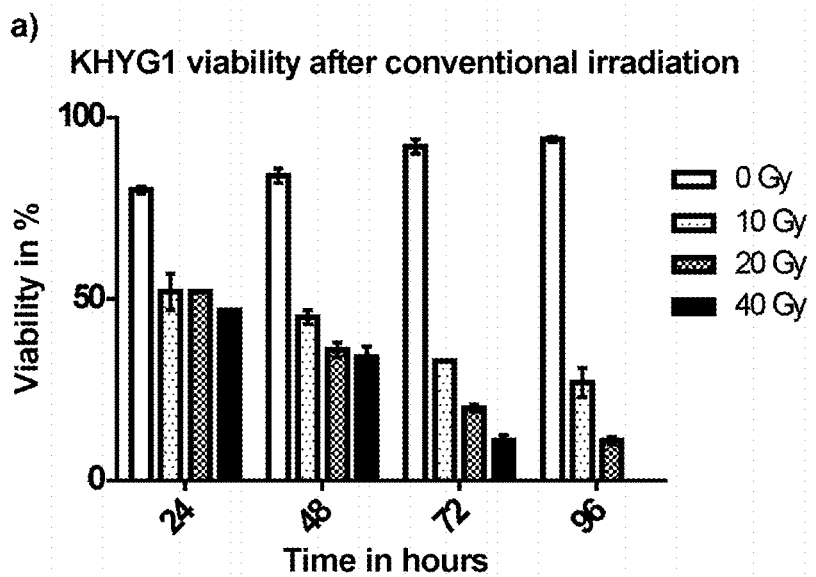
Figure 10:
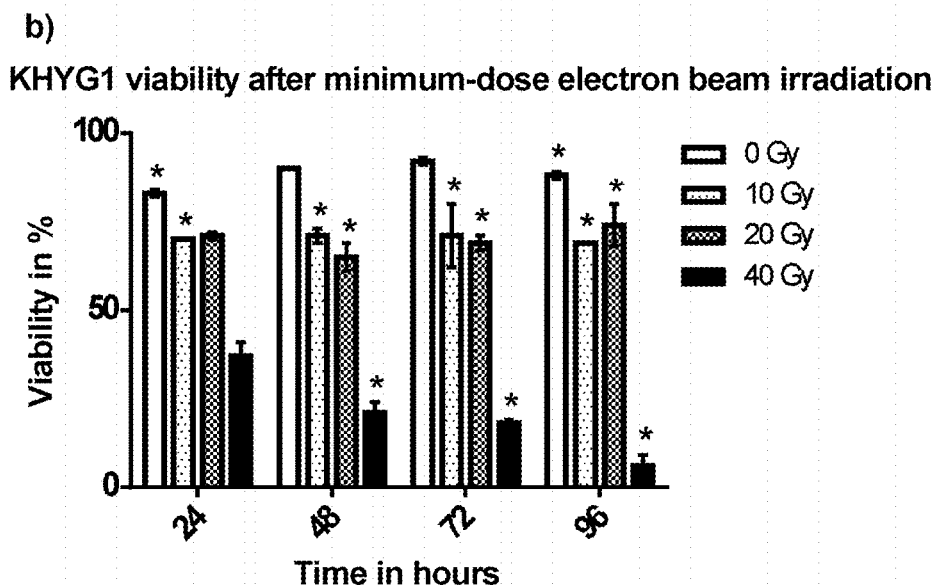

FIG. 10: Viability of KHYG1 after conventional irradiation or minimum-dose electron beam irradiation. The NK cell line KHYG1 was irradiated with (a) conventional x-ray irradiation (doses: 10, 20, and 40 Gy; device: SARRP, Xstrahl Limited, UK) or (b) minimum-dose electron beam irradiation. Electron irradiation was carried out under the following conditions: dose rate: approx. 300 Gy/sec., calculated doses: 0, 10, 20, and 40 Gy. The cells were seeded at a density of 1 mill. cells/ml onto NK cell medium in a 6-well plate with a flat bottom. Cell viability was measured using the BD Accuri™ C6. Viability was observed over four days (24, 48, 72, and 96 hours). The conventional irradiation data were calculated from an experiment with duplicates and were expressed as mean value ±SD. The data for minimum-dose electron beam irradiation were calculated from three independent experiments and were expressed as mean value ±SD, n=3. Compared to the conventional irradiation data, statistical significance was reached at $p<0.05$ (*) and calculated by the unpaired two-sample t-test.

Figure 11:
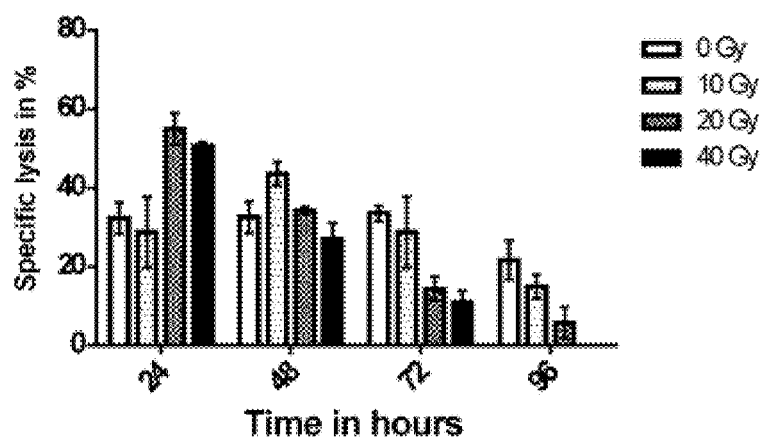
Figure 11:
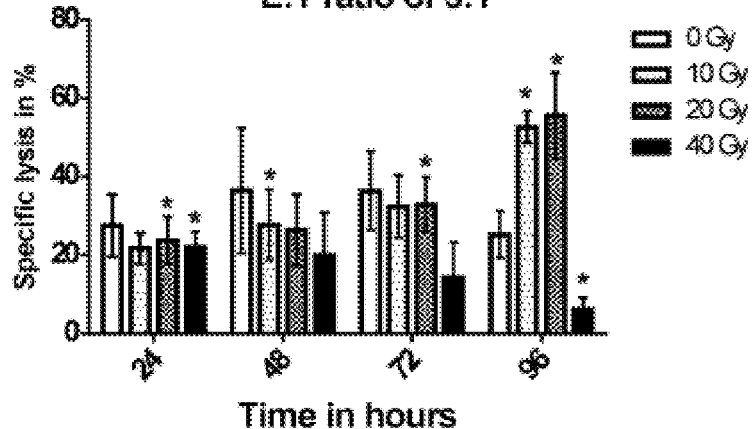

FIG. 11: Cytotoxic capacity of KHYG1 after conventional irradiation and minimum-dose electron beam irradiation. Ratio of effector cells to target cells 5:1. The NK cell line KHYG1 was irradiated with (a) conventional x-ray irradiation (x-ray irradiation (doses: 10, 20, and 40 Gy; device: SARRP, Xstrahl Limited, UK) or (b) minimum-dose electron beam irradiation ("ebeam"). Electron irradiation was carried out under the following conditions: dose rate: approx. 300 Gy/sec., calculated doses: 0, 10, 20, and 40 Gy. Specific lysis was determined over four days (24, 48, 72, and 96 hours). For the europium cytotoxicity assay, KHYG1 was co-cultivated for two hours with the target cell line K562 at an E:T ratio of 5:1 in NK cell medium. The conventional irradiation data were calculated from an experiment with duplicates and were expressed as mean value ±SD. The data for minimum-dose electron beam irradiation were calculated from three independent experiments with triplicates and were expressed as mean value ±SD. Compared to the conventional irradiation data, statistical significance was reached at $p<0.05$ (*) and calculated by the unpaired two-sample t-test. Abbreviation: E:T: effector cells to target cells.

Figure 12:
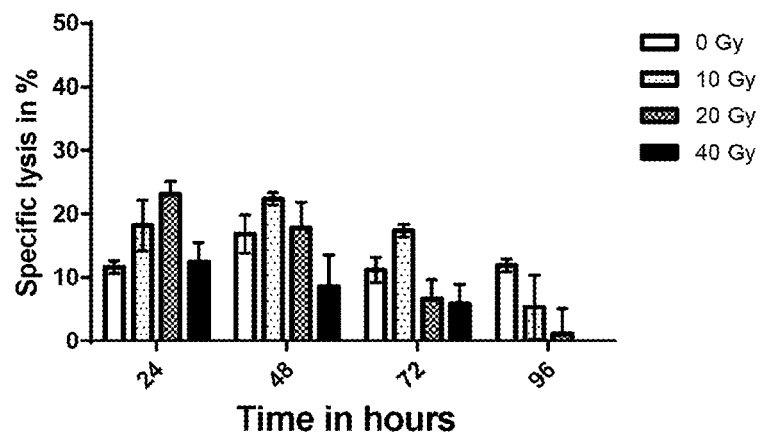
Figure 12:
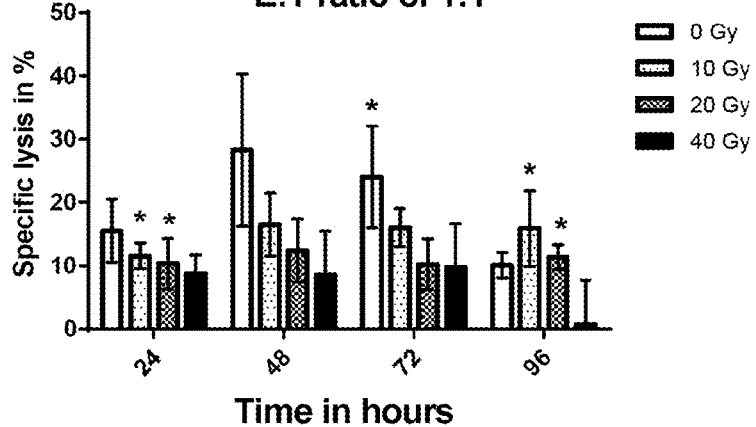

FIG. 12: Cytotoxic capacity of KHYG1 after conventional irradiation and minimum-dose electron beam irradiation. Ratio of effector cells to target cells 1:1. The NK cell line KHYG1 was irradiated with (a) conventional x-ray irradiation (doses: 10, 20, and 40 Gy; device: SARRP, Xstrahl Limited, UK) or (b) minimum-dose electron irradiation. Electron irradiation was carried out under the following conditions: dose rate: approx. 300 Gy/sec., calculated doses: 0, 10, 20, and 40 Gy. Specific lysis was determined over four days (24, 48, 72, and 96 hours). For the europium cytotoxicity assay, KHYG1 was co-cultivated for two hours with the target cell line K562 at an E:T ratio of 1:1 in NK cell medium. The conventional irradiation data were calculated from an experiment with duplicates and were expressed as mean value ±SD. The data for minimum-dose electron beam irradiation were calculated from three independent experiments with triplicates and were expressed as mean value ±SD. Compared to the conventional irradiation data, statistical significance was reached at $p<0.05$ (*) and calculated by the unpaired two-sample t-test. Abbreviation: E:T: effector cells to target cells.

EXAMPLES

Methods

The suspensor cell lines NK-92 (natural killer lymphoma, DSMZ #: ACC488) and KHYG-1 (natural killer leukemia, DSMZ #: ACC 725; obtained from the DSMZ, Braunschweig, Germany) were expanded under conditions of 37° C., 5% $CO_2$, and 100% humidity in culture medium (RPMI 1640 [Life Technologies, Karlsruhe] with 20% FKS [Fisher Scientific, Schwerte], 2 mM glutamine [Fisher Scientific, Schwerte], 100 mM HEPES [Fisher Scientific, Schwerte], 1% MEM amino acids [Fisher Scientific, Schwerte], 100 U/ml penicillin-streptomycin [Life Technologies, Karlsruhe], and 100 U/ml IL-2 [ReproTech, Hamburg, #200-02]). The cell count was maintained for cultivation or expansion at 0.2-1×$10^6$ cells/ml of medium.

70 µl of a 1×$10^7$ cells/ml cell suspension was irradiated for each test. For this purpose, the cell count and viability were determined prior to irradiation by trypan blue counting. Specifically, 10 µl of the cell suspension in medium (see above) was mixed with 10 µl of a 0.5% trypan blue solution (0.5 g trypan blue [Thomas Geyer, Renningen] in 100 ml of DPBS buffer [Fisher Scientific, Schwerte]). The mixture was incubated for approx. 2 minutes at 37° C. and counted using a Neubauer cell counting chamber [Dr. Ilona Schubert Laborfachhandel, Leipzig].

In this process, 10 µl of the mixture was added to the chamber under a glass cover, filling the chamber with the colored mixture. Evaluation was carried out using a 10× objective under a cell culture transmission microscope (Axio, Zeiss, Jena). The viable cells are morphologically round and colorless, while dead cells are also round and dyed purple. The cell count is the mean value of the cell count in the four large squares multiplied by the dilution factor (here: 0.5), the volume of the original cell suspension, and the counting chamber-specific factor $10^4$.

Before the experiment was carried out, the cells were adjusted to the desired cell density, harvested or pelleted by centrifugation at 300×g [Fisher Scientific, Schwerte], and taken up in 70 µl each of DPBS. Immediately prior to irradiation, 70 µl of the cell suspension with 1×$10^7$ cells was pipetted into the center of a petri dish [Corning® Primaria™ Easy-Grip Dish, Corning B.V. Life Sciences, Amsterdam, the Netherlands] and overcoated with an OPP (oriented polypropylene) film with a diameter of 3 cm in order to produce a confluent cell monolayer prior to irradiation. Biological duplicates were irradiated.

The petri dish was placed on a sample holder without a lid and covered with film in order to ensure a certain degree of sterility. The cells were irradiated with a minimum dose in the range of approx. 20±10 Gy (referred to in the following as the "minimum dose") and with 5, 10, 50, and 100 times this minimum dose. Irradiation was therefore carried out with doses in the range of approx. 20 Gy to 2000 Gy (calculated).

Irradiation was carried out under the following conditions:

Dose rate: approx. 300 Gy/sec (calculated).
Irradiation time: between 0.066 and 6.6 sec.
Immediately after irradiation, the cells were dissolved under the OPP film with approx. 100 µl of a trypsin/0.5% EDTA solution [Fisher Scientific, Schwerte], washed with DPBS, and their viability was then determined by trypan blue staining. After this, the cells were mixed with medium, transferred to a new well for further cultivation, and treated according to the cultivation conditions (see above). Viability and cell count were determined at intervals of 6 h, 24 h, 48 h, 72 h, 96 h, and 144 h.

For the test of FIG. 5, the proliferation of NK92 was determined after conventional irradiation at a low dose rate or minimum-dose electron beam irradiation at a high dose rate. The NK cell line NK92 was irradiated with conventional x-ray irradiation (doses: 10, 20, and 40 Gy; device: SARRP, Xstrahl Limited, UK) ("x-ray") or minimum-dose electron beam irradiation ("ebeam"). Electron irradiation was carried out under the following conditions: dose rate: approx. 300 Gy/sec (calculated), irradiation time: between 0.033 and 6.6 sec, calculated doses: 0, 10, 20, and 40 Gy. The cells were seeded immediately after irradiation at a density of 1 mill. cells/ml onto NK cell medium in a 6-well plate with a flat bottom. The cells were counted by trypan blue staining. Proliferation was observed over four days (24, 48, 72, and 96 hours). The count after 24 hours of irradiation was taken as a reference value. The conventional irradiation data were calculated from an experiment with triplicates and were expressed as mean value ±SEM. The data for minimum-dose electron beam irradiation were calculated from three independent experiments and were expressed as mean value ±SEM, n=3.

For the test of FIG. 6, the viability of NK92 was determined after conventional irradiation at a low dose rate or minimum-dose electron beam irradiation at a high dose rate. The NK cell line NK92 was irradiated with (a) conventional x-ray irradiation (doses: 10, 20, and 40 Gy; device: SARRP, Xstrahl Limited, UK) or (b) minimum-dose electron beam irradiation. Electron irradiation was carried out under the following conditions: dose rate: approx. 300 Gy/sec (calculated), irradiation time: between 0.033 and 6.6 sec, calculated doses: 0, 10, 20, and 40 Gy. The cells were seeded at a density of 1 mill. cells/ml onto NK cell medium in a 6-well plate with a flat bottom. Cell viability was measured using the BD Accuri™ C6. Viability was observed over four days (24, 48, 72, and 96 hours). The conventional irradiation data were calculated from an experiment with duplicates and were expressed as mean value ±SD. The data for minimum-dose electron beam irradiation were calculated from three independent experiments and were expressed as mean value ±SD, n=3. Compared to the conventional irradiation data, statistical significance was reached at $p<0.05$ (*) and calculated by the unpaired two-sample t-test.

For the test of FIG. 7, the cytotoxic capacity of NK92 was determined after conventional irradiation at a low dose rate and minimum-dose electron beam irradiation at a high dose rate, with a ratio of effector cells to target cells of 5:1. The NK cell line NK92 was irradiated with (a) conventional x-ray irradiation (doses: 10, 20, and Gy; device: SARRP, Xstrahl Limited, UK) or (b) minimum-dose electron beam irradiation. Electron irradiation was carried out under the following conditions: dose rate: approx. 300 Gy/sec (calculated), irradiation time: between 0.033 and 6.6 sec, calculated doses: 0, 10, 20, and 40 Gy. Specific lysis was determined over four days (24, 48, 72, and 96 hours). For the europium cytotoxicity assay, NK92 was co-cultivated for two hours with the target cell line K562 at an E:T ratio of 5:1 in NK cell medium. The conventional irradiation data were calculated from an experiment with duplicates and were expressed as mean value ±SD. The data for minimum-dose electron beam irradiation were calculated from three independent experiments with triplicates and were expressed as mean value ±SD. Compared to the conventional irradiation data, statistical significance was reached at $p<0.05$ (*) and calculated by the unpaired two-sample t-test. Abbreviation: E:T: effector cells to target cells.

For the test of FIG. 8, the cytotoxic capacity of NK92 was determined after conventional irradiation at a low dose rate and minimum-dose electron beam irradiation at a high dose rate, with a ratio of effector cells to target cells of 1:1. The NK cell line NK92 was irradiated with (a) conventional x-ray irradiation (doses: 10, 20, and 40 Gy; device: SARRP, Xstrahl Limited, UK) or (b) minimum-dose electron beam irradiation. Electron irradiation was carried out under the following conditions: dose rate: approx. 300 Gy/sec (calculated), irradiation time: between 0.033 and 6.6 sec, calculated doses: 0, 10, 20, and 40 Gy. Specific lysis was determined over four days (24, 48, 72, and 96 hours). For the europium cytotoxicity assay, NK92 was co-cultivated for two hours with the target cell line K562 at an E:T ratio of 1:1 in NK cell medium. The conventional irradiation data were calculated from an experiment with duplicates and were expressed as mean value ±SD. The data for minimum-dose electron beam irradiation were calculated from three independent experiments with triplicates and were expressed as mean value ±SD. Compared to the conventional irradiation data, statistical significance was reached at $p<0.05$ (*) and calculated by the unpaired two-sample t-test.

For the test of FIG. 9, the proliferation of KHYG1 was determined after conventional irradiation at a low dose rate or minimum-dose electron beam irradiation at a high dose rate. The NK cell line KHYG1 was irradiated with conventional x-ray irradiation (doses: 10, 20, and 40 Gy; device: SARRP, Xstrahl Limited, UK) ("x-ray") or minimum-dose electron beam irradiation ("ebeam"). Electron irradiation was carried out under the following conditions: dose rate: approx. 300 Gy/sec, calculated doses: 0, 10, 20, and 40 Gy. The cells were seeded immediately after irradiation at a density of 1 mill. cells/ml onto NK cell medium in a 6-well plate with a flat bottom. The cells were counted by trypan blue staining. Proliferation was observed over four days (24, 48, 72, and 96 hours). The count after 24 hours of irradiation was taken as a reference value. The conventional irradiation data were calculated from an experiment with triplicates and were expressed as mean value ±SEM. The data for minimum-dose electron beam irradiation were calculated from three independent experiments and were expressed as mean value ±SEM, n=3.

For the test of FIG. 10, the viability of KHYG1 was determined after conventional irradiation at a low dose rate or minimum-dose electron beam irradiation at a high dose rate. The NK cell line KHYG1 was irradiated with (a) conventional x-ray irradiation (doses: 10, 20, and 40 Gy; device: SARRP, Xstrahl Limited, UK) or (b) minimum-dose electron beam irradiation. Electron irradiation was carried out under the following conditions: dose rate: approx. 300 Gy/sec, calculated doses: 0, 10, 20, and 40 Gy. The cells were seeded at a density of 1 mill. cells/ml onto NK cell medium in a 6-well plate with a flat bottom. Cell viability was measured using the BD Accuri™ C6. Viability was observed over four days (24, 48, 72, and 96 hours). The conventional irradiation data were calculated from an experiment with duplicates and were expressed as mean value ±SD. The data for minimum-dose electron beam irradiation were calculated from three independent experiments and were expressed as mean value ±SD, n=3. Compared to the conventional irradiation data, statistical significance was reached at $p<0.05$ (*) and calculated by the unpaired two-sample t-test.

For the test of FIG. 11, the cytotoxic capacity of KHYG1 was determined after conventional irradiation at a low dose rate and minimum-dose electron beam irradiation at a high dose rate, with a ratio of effector cells to target cells of 5:1. The NK cell line KHYG1 was irradiated with (a) conventional x-ray irradiation (doses: 10, 20, and 40 Gy; device: SARRP, Xstrahl Limited, UK) or (b) minimum-dose electron beam irradiation. Electron irradiation was carried out under the following conditions: dose rate: approx. 300 Gy/sec, calculated doses: 0, 10, 20, and 40 Gy. Specific lysis was detected over four days (24, 48, 72, and 96 hours). For the europium cytotoxicity assay, KHYG1 was co-cultivated for two hours with the target cell line K562 at an E:T ratio of 5:1 in NK cell medium. The conventional irradiation data were calculated from an experiment with duplicates and were expressed as mean value ±SD. The data for minimum-dose electron beam irradiation were calculated from three independent experiments with triplicates and were expressed as mean value ±SD. Compared to the conventional irradiation data, statistical significance was reached at $p<0.05$ (*) and calculated by the unpaired two-sample t-test.

For the test of FIG. 12, the cytotoxic capacity of KHYG1 was determined after conventional irradiation at a low dose rate and minimum-dose electron beam irradiation at a high dose rate, with a ratio of effector cells to target cells of 1:1. The NK cell line KHYG1 was irradiated with (a) conventional x-ray irradiation (doses: 10, 20, and 40 Gy; device: SARRP, Xstrahl Limited, UK) or (b) minimum-dose electron beam irradiation. Electron irradiation was carried out under the following conditions: dose rate: approx. 300 Gy/sec, calculated doses: 0, 10, 20, and 40 Gy. Specific lysis was determined over four days (24, 48, 72, and 96 hours). For the europium cytotoxicity assay, KHYG1 was co-cultivated for two hours with the target cell line K562 at an E:T ratio of 1:1 in NK cell medium. The conventional irradiation data were calculated from an experiment with duplicates and were expressed as mean value ±SD. The data for minimum-dose electron beam irradiation were calculated from three independent experiments with triplicates and were expressed as mean value ±SD.

Compared to the conventional irradiation data, statistical significance was reached at $p<0.05$ (*) and calculated by the unpaired two-sample t-test.

In the conventional irradiation methods with gamma rays or x-rays known from the prior art, a low dose rate is used; i.e., a specified dose is applied over a long period of time.

Results

In the tests, it was possible to produce a thin liquid film of a cell suspension that was subjected to irradiation with electron beams at a high dose rate. Surprisingly, limitation of proliferation activity of the respective cellular component was confirmed, with largely maintained viability (FIGS. 2 and 3).

It can also be seen from FIG. 4 that irradiation with electron beams at a high dose rate is superior with respect to the viability of the cells after irradiation compared to the published results for viability of conventionally irradiated cells (gamma irradiation, 10 Gy, modified according to Tam et al. 1999 for NK-92 and Suck et al. 2006 for KHYG-1) irradiated at a lower dose rate, at the same doses respectively.

Moreover, FIGS. 5 to 12 show that irradiation according to the invention with electron beams at a high dose rate is superior to conventional irradiation with x-rays at 10 Gy, 20 Gy or 40 Gy and a lower dose rate, with respect both to the viability of the cells and the desired biological activity of cytotoxicity, using the same dose respectively.

The invention claimed is:

1. A method of irradiating a population of mammalian cells comprising at least one target mammalian cell with electron beams and/or x-rays, the method comprising:
   (i) irradiating a composition comprising a population of mammalian cells in vitro with electron beams and/or x-rays, wherein the population of mammalian cells contains at least one target mammalian cell, wherein the dose rate of irradiation is in the range of 5 Gy/sec to $10^7$ Gy/sec, and wherein the dose is in the range of 1 Gy to 300 Gy; and
   (ii) optionally, isolating or enriching viable target mammalian cells from the population of mammalian cells.

2. A method of for producing an agent comprising at least one treated viable target mammalian cell that is suitable for administration to an individual and/or for producing treated viable target mammalian cells that are suitable for producing a cellular agent for administration to an individual, the method comprising:
   (i) irradiating a composition comprising a population of mammalian cells in vitro with electron beams and/or x-rays, wherein the population of mammalian cells contains at least one target mammalian cell, wherein the irradiation dose rate is in the range of 5 Gy/sec to $10^7$ Gy/sec, and wherein the dose is in the range of 1 Gy to 300 Gy; and
   (ii) optionally, isolating or enriching viable target mammalian cells from the population of mammalian cells.

3. The method according to claim 1, wherein (i) the population of mammalian cells comprises target mammalian cells, or
   (ii) the population of mammalian cells contains at least one target mammalian cell and one or a plurality of other mammalian cells.

4. The method according to claim 3, wherein
   (a) the population of mammalian cells comprises a mixture of at least 2 different primary mammalian cells, or wherein the population of mammalian cells is a cellular transplant or a mixture of immune cells or a body fluid, and/or
   (c) the population of mammalian cells comprises one or a plurality of cell lines, and/or
   (b) the target mammalian cell is a proliferating, hyperproliferative or immortalized target mammalian cell, or wherein the target mammalian cell is a cancer cell, a cancer cell line and/or an immune cell.

5. The method according to claim 1, wherein the population of mammalian cells or the target mammalian cells is/are suitable for administration to an individual and/or is/are suitable for producing a cellular agent for administration to an individual after irradiation.

6. The method according to claim 1, wherein the population of mammalian cells or the target mammalian cells is/are suitable for therapeutic, preventive or cosmetic administration to an individual, and/or is/are suitable for producing a cellular therapeutic, preventive or cosmetic agent for administration to an individual, or wherein the population of mammalian cells or the target mammalian cells is/are suitable for administration to an individual for the treatment and/or prevention of a hyperproliferative disease, immune disease or chronic degenerative disease and/or the agent comprising at least one treated viable target mammalian cell is a transplant, a hematopoietic stem cell transplant, a vaccine, a cytotoxic agent, or an apheresis product.

7. The method according to claim 1, wherein
   (a) the dose is in the range of 1 Gy to 100 Gy,
   (b) the dose rate is in the range of 10 Gy/sec to $10^3$ Gy/sec,
   (c) the irradiation time is in the range of between 0.1 msec and 10 sec, or
   (d) the irradiation time is in the range of between 10 msec and 8 sec.

8. The method according to claim 1, wherein the composition comprising the population of mammalian cells is in the form of a thin layer in step (i).

9. The method according to claim 8, wherein the thin layer has a thickness of between 0.5 μm and 3 cm.

10. The method according to claim 1, wherein the composition comprising the population of mammalian cells in step (i) is frozen, a gel, a sol, or a liquid.

11. The method according to claim 1, wherein the composition comprising the population of mammalian cells of step (i), is of a form selected from a cell suspension, an adherent cell layer on a solid carrier, on a solid carrier, a thin liquid stream, or an aerosol.

12. The method according to claim 1, wherein irradiation is carried out with electron beams and the electron beams are accelerated with an acceleration energy of between 80 keV and 10 MeV, or with an acceleration energy of between 80 keV and 300 keV.

13. The method according to claim 1, wherein
   (a) the composition comprising the population of mammalian cells comprises at least one viable target mammalian cell after irradiation, and
   (b) the target mammalian cell(s) of the composition show a reduced proliferation capacity after irradiation, and optionally,
   (c) the target mammalian cell(s) of the composition show(s) biological activity after irradiation, wherein the biological activity is selected from cytotoxicity, immunogenicity, immunosuppression, and/or immune tolerance induction.

14. The method of claim 4, wherein the cell line is a natural killer (NK) cell line, a T cell line, or a genetically modified cell line, and/or the immune cells are NK cells, T cells, or genetically modified immune cells.

15. The method of claim 11, wherein the population of mammalian cells in irradiating step (i), contains no tissue.

16. The method of claim 2, wherein irradiation is carried out with electron beams and the electron beams are accelerated with an acceleration energy of between 80 keV and 10 MeV, or with an acceleration energy of between 80 keV and 300 keV.

17. The method of claim 13, wherein the target mammalian cell(s) is/are (a) hyperproliferative or immortalized cell(s) and the proliferation capacity after irradiation is reduced by 100%.

* * * * *